(12) United States Patent
Lim et al.

(10) Patent No.: US 11,938,115 B2
(45) Date of Patent: Mar. 26, 2024

(54) BENZOSELENOPHENE-BASED COMPOUND, PHARMACEUTICAL COMPOSITION CONTAINING SAME, AND ANTIBODY-DRUG CONJUGATE

(71) Applicant: AIMED BIO INC., Seoul (KR)

(72) Inventors: Dongyeol Lim, Seoul (KR); Min Cheol Kim, Seoul (KR); Amol Mhetre, Seoul (KR); Do-Hyun Nam, Seoul (KR)

(73) Assignee: AIMED BIO INC., Seoul (KR)

( * ) Notice: Subject to any disclaimer, the term of this patent is extended or adjusted under 35 U.S.C. 154(b) by 75 days.

(21) Appl. No.: 17/815,958

(22) Filed: Jul. 29, 2022

(65) Prior Publication Data

US 2022/0380360 A1 Dec. 1, 2022

Related U.S. Application Data

(63) Continuation of application No. PCT/KR2021/001082, filed on Jan. 27, 2021.

(30) Foreign Application Priority Data

Jan. 30, 2020 (KR) .................. 10-2020-0011222

(51) Int. Cl.
*A61K 31/404* (2006.01)
*A61K 47/54* (2017.01)
*A61K 47/68* (2017.01)
*A61P 35/00* (2006.01)
*C07D 421/06* (2006.01)

(52) U.S. Cl.
CPC .......... *A61K 31/404* (2013.01); *A61K 47/545* (2017.08); *A61K 47/6803* (2017.08); *A61K 47/6855* (2017.08); *A61K 47/6857* (2017.08); *A61K 47/6859* (2017.08); *A61K 47/6861* (2017.08); *A61K 47/6863* (2017.08); *A61K 47/6865* (2017.08); *A61K 47/6867* (2017.08); *A61K 47/6869* (2017.08); *A61P 35/00* (2018.01); *C07D 421/06* (2013.01)

(58) Field of Classification Search
CPC .... C07D 421/00; C07D 421/06; A61K 31/28; A61K 31/403; A61K 47/68; A61P 35/00
See application file for complete search history.

(56) References Cited

U.S. PATENT DOCUMENTS

| 4,975,278 | A | 12/1990 | Senter |
| 11,576,896 | B2* | 2/2023 | Lim .................. A61K 47/6803 |
| 2014/0213790 | A1* | 7/2014 | Lim .................... C07D 517/04 548/425 |
| 2017/0020840 | A1 | 1/2017 | Chaplin |

FOREIGN PATENT DOCUMENTS

| CN | 101415679 A | | 4/2009 | |
| CN | 101795711 A | | 8/2010 | |
| KR | 10-2013-0034638 A | | 4/2013 | |
| KR | 10-2013-0064018 A | | 6/2013 | |
| KR | 10-2017-0041562 A | | 4/2017 | |
| KR | 1020170041562 A | * | 4/2017 | ........... C07D 421/06 |
| WO | 9732850 A1 | | 9/1997 | |
| WO | 2007087684 A1 | | 8/2007 | |
| WO | WO-2007089149 A2 | * | 8/2007 | ........... A61K 31/403 |
| WO | WO-2013048177 A2 | * | 4/2013 | ........... A61K 31/095 |

OTHER PUBLICATIONS

International Search Report of PCT/KR2021/001082 dated May 4, 2021.
Mhetre, A. B. et al., "Synthesis and biological evaluation of potent benzoselenophene and heteroaromatic analogues of (S)-1-(chloromethyl)-8-methoxy-2,3-dihydro-1H-benzo[e]indol-5-ol (seco-MCBI)", RSC advances, 2019, vol. 9, No. 50, pp. 29023-29036.
Mhetre, A. B. et al., "Synthesis and anticancer activity of benzoselenophene and heteroaromatic derivatives of 1,2,9,9atetrahydrocyclopropa[c]benzo[e]indol-4-one (CBI)", Organic & biomolecular chemistry, 2017, vol. 15, No. 5, pp. 1198-1208.
Gillian Payne, "Progress in immunoconjugate cancer therapeutics", Cancer Cell, Mar. 2003, vol. 3.
Trail et al., "Monoclonal antibody drug immunoconjugates for targeted treatment of cancer", Cancer Immunol Immunother (2003), vol. 52, pp. 328-337.
Syrigos et al., "Antibody directed enzyme prodrug therapy (ADEPT): a review of the experimental and clinical considerations", Anticancer Research.
Niculescu-Duvaz et al., "Antibody-directed enzyme prodrug therapy(ADEPT): a review", Advanced Drug Delivery Reviews 1997, vol. 26, pp. 151-172.

* cited by examiner

Primary Examiner — Theodore R. Howell
Assistant Examiner — George W Kosturko
(74) Attorney, Agent, or Firm — Shih IP Law Group, PLLC

(57) ABSTRACT

The present disclosure relates to a benzoselenophene-based compound, a method of preparing the benzoselenophene-based compound, and a pharmaceutical composition and antibody-drug conjugate including the benzoselenophene-based compound.

20 Claims, 20 Drawing Sheets

[Fig. 1]
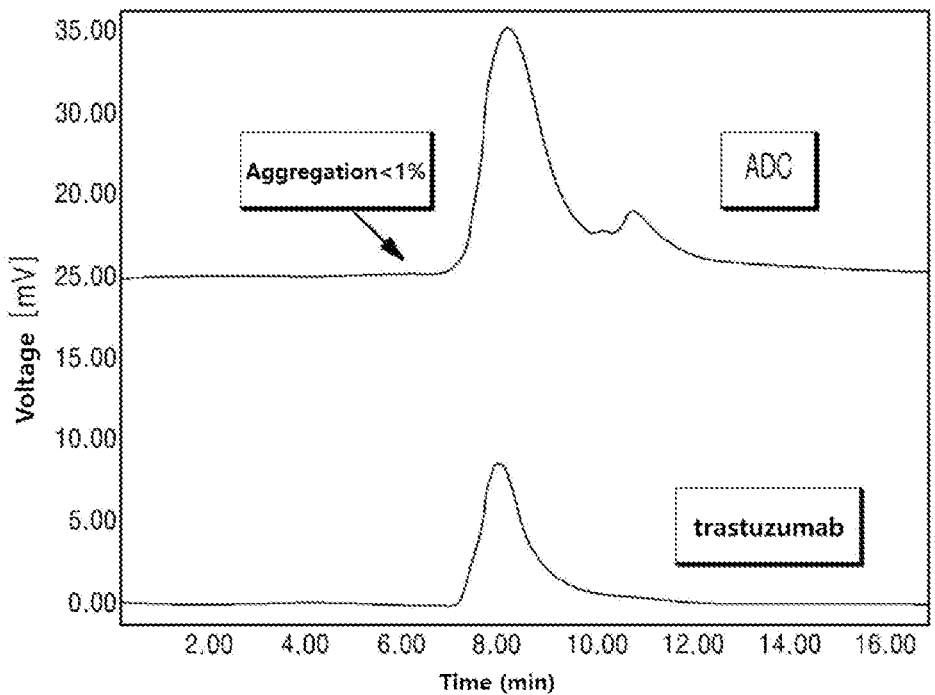
[Fig. 2]
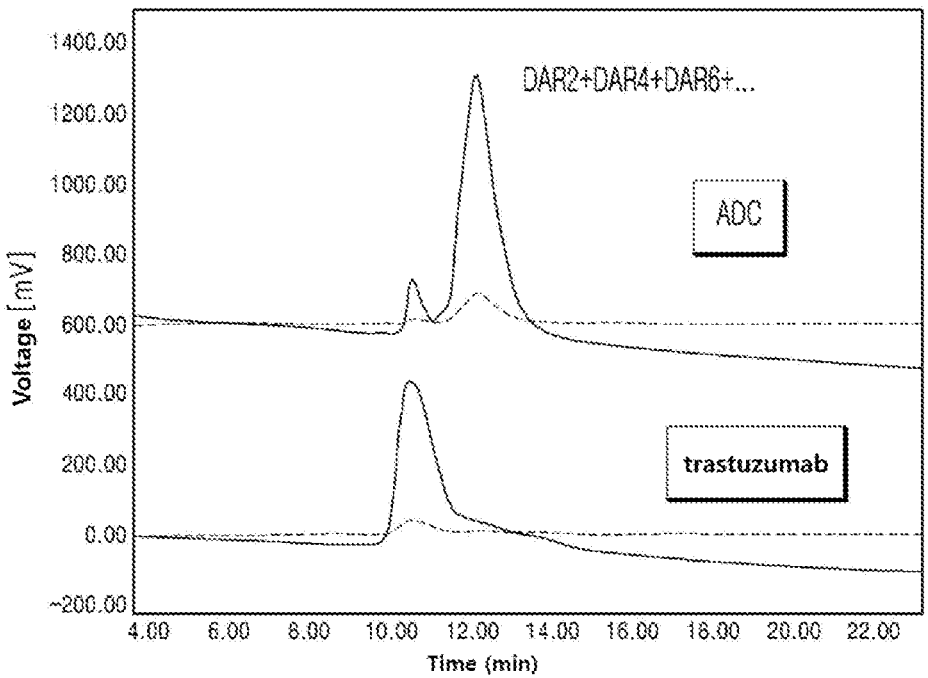

[Fig. 3]
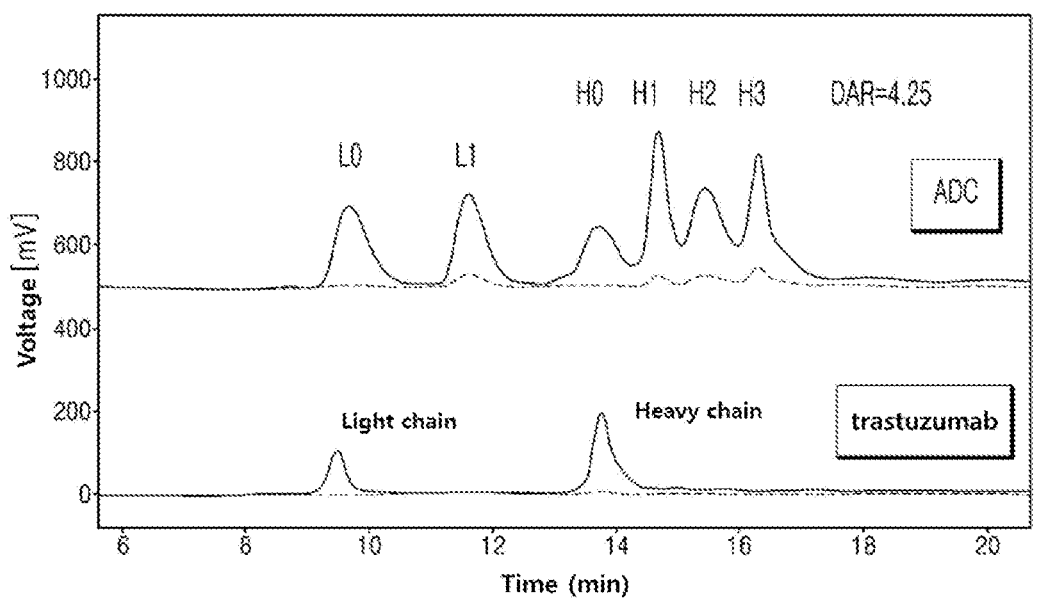

[Fig. 4]
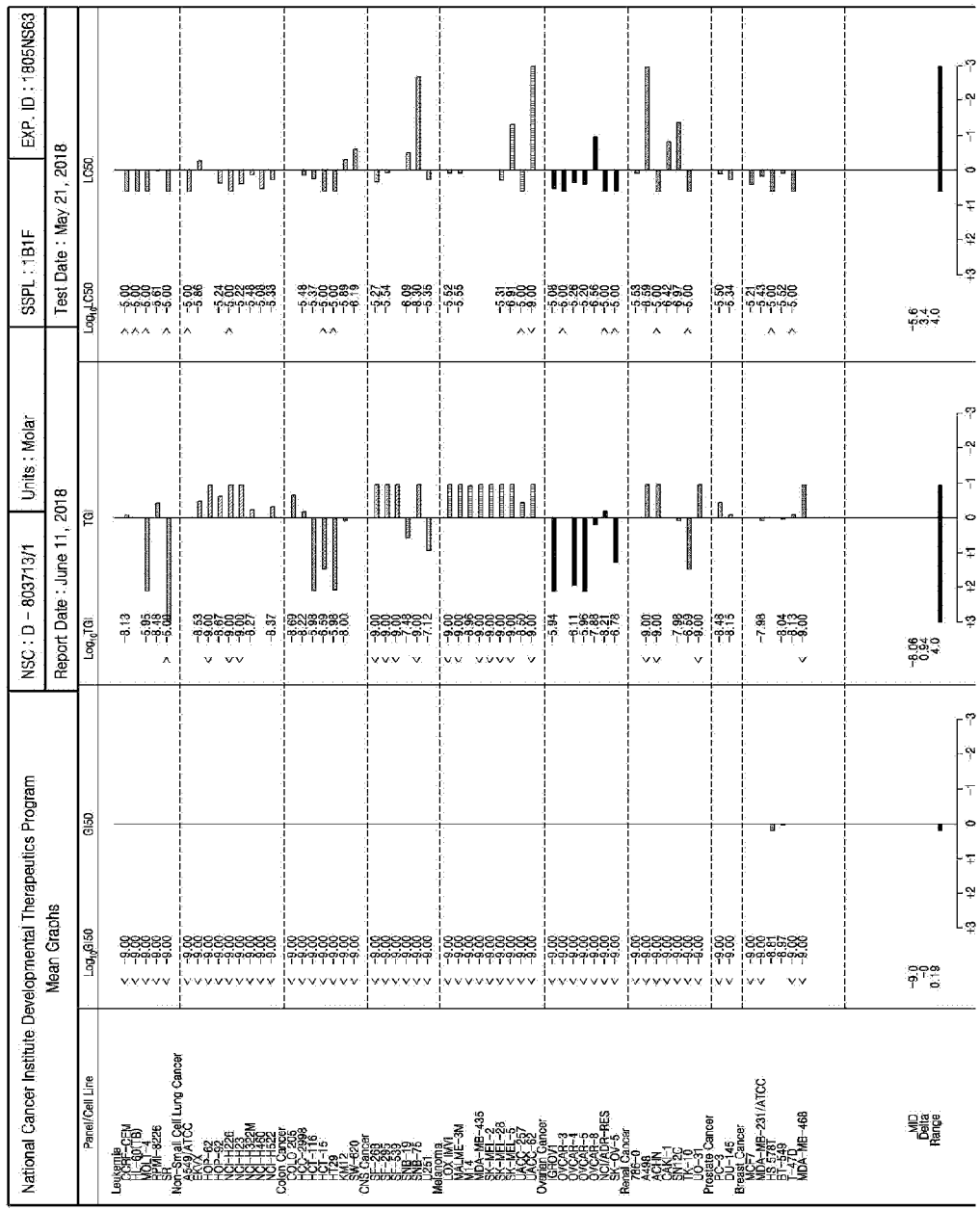

[Fig. 5a]
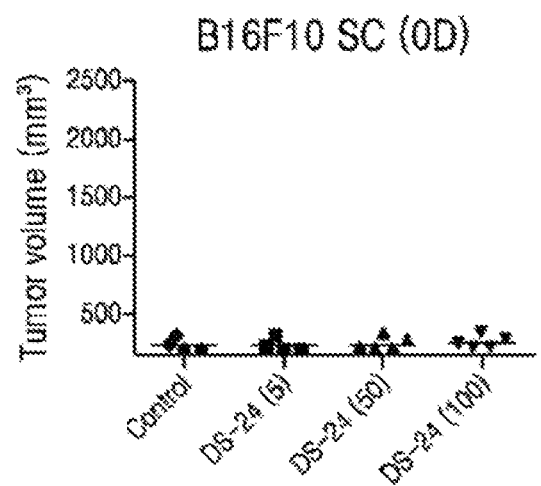
[Fig. 5b]
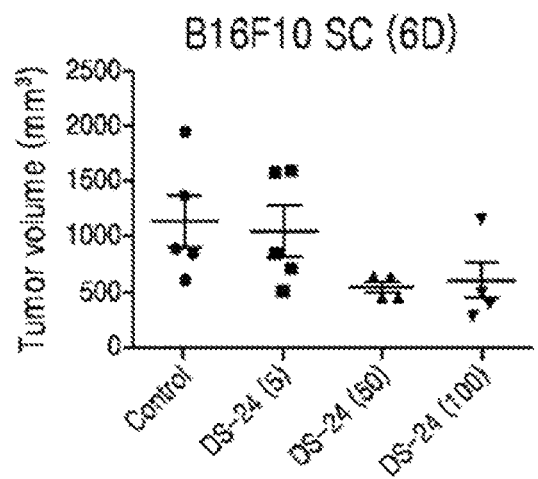

[Fig. 5c]
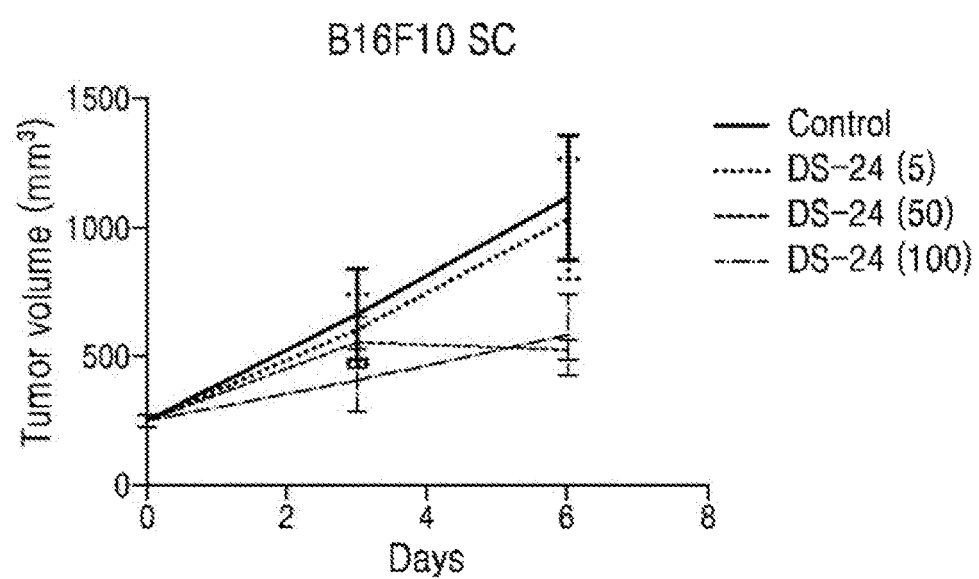

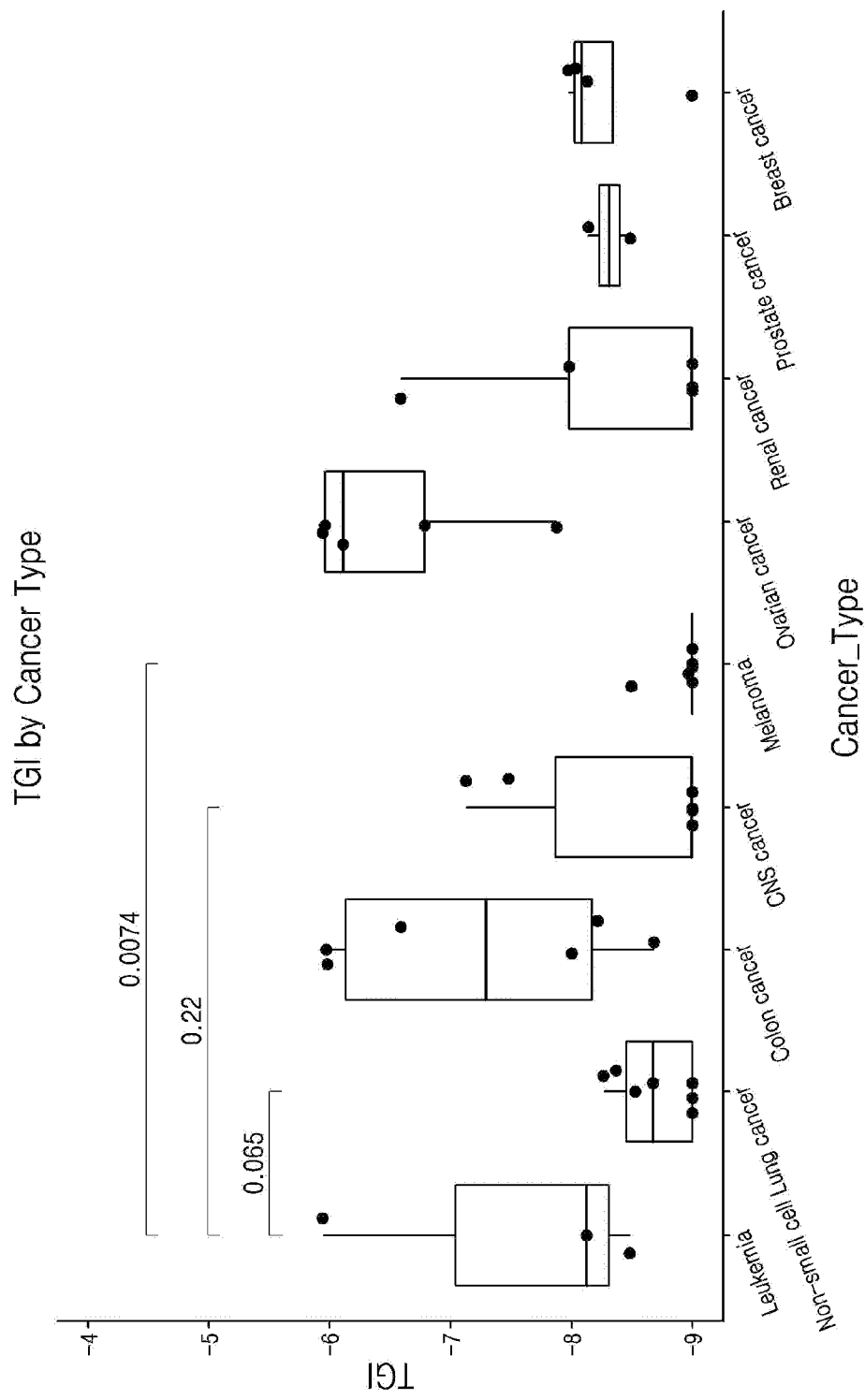
[Fig. 6]

[Fig. 7a]
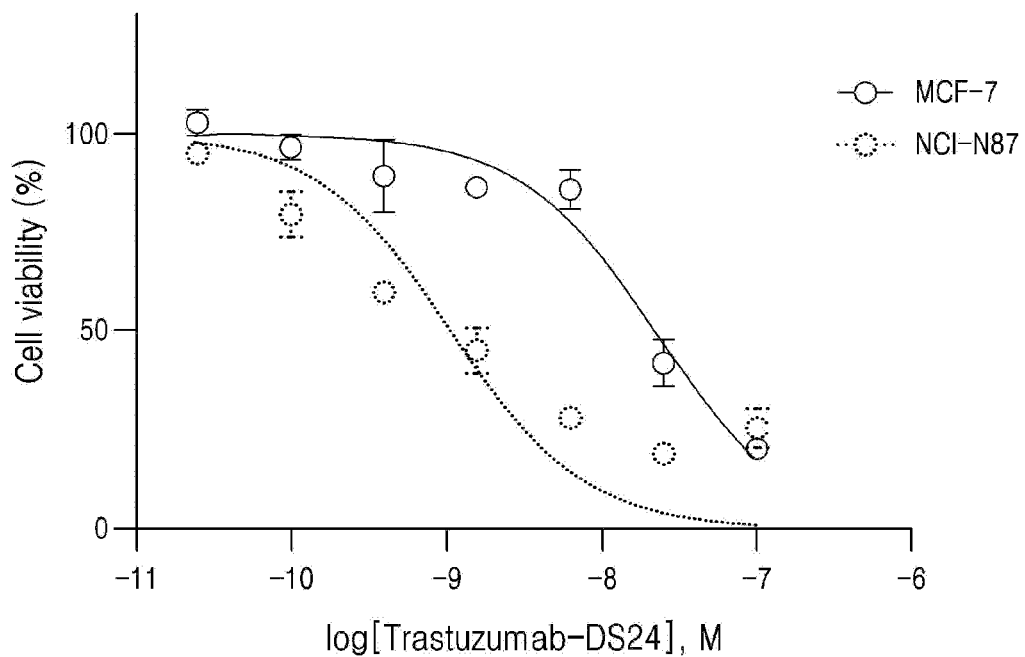
[Fig. 7b]
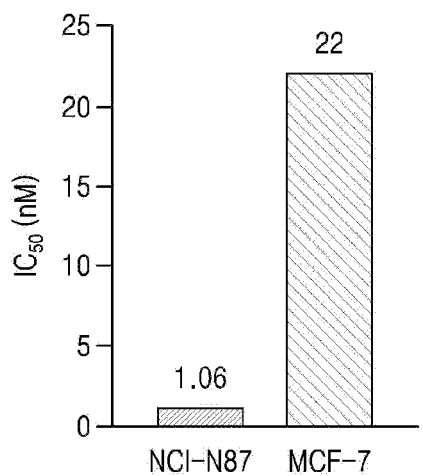

[Fig. 8a]
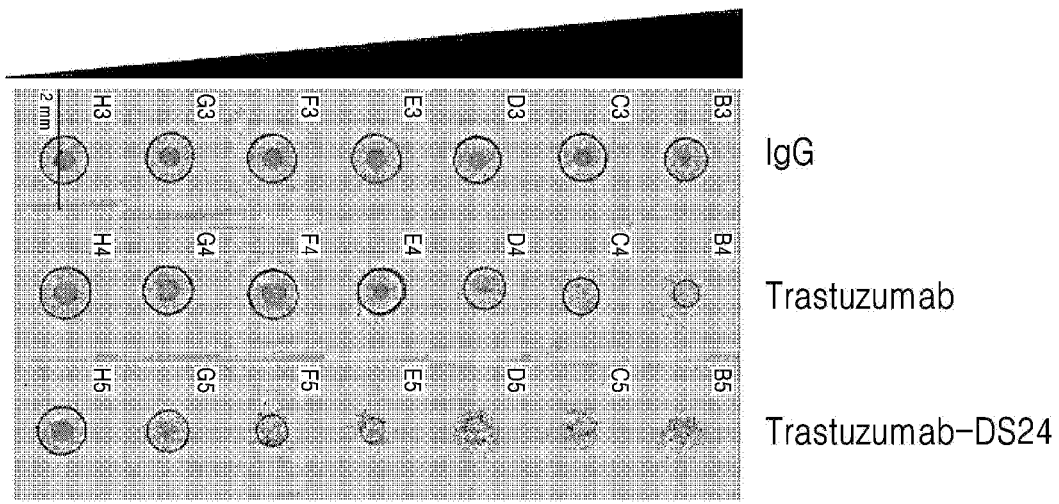
[Fig. 8b]
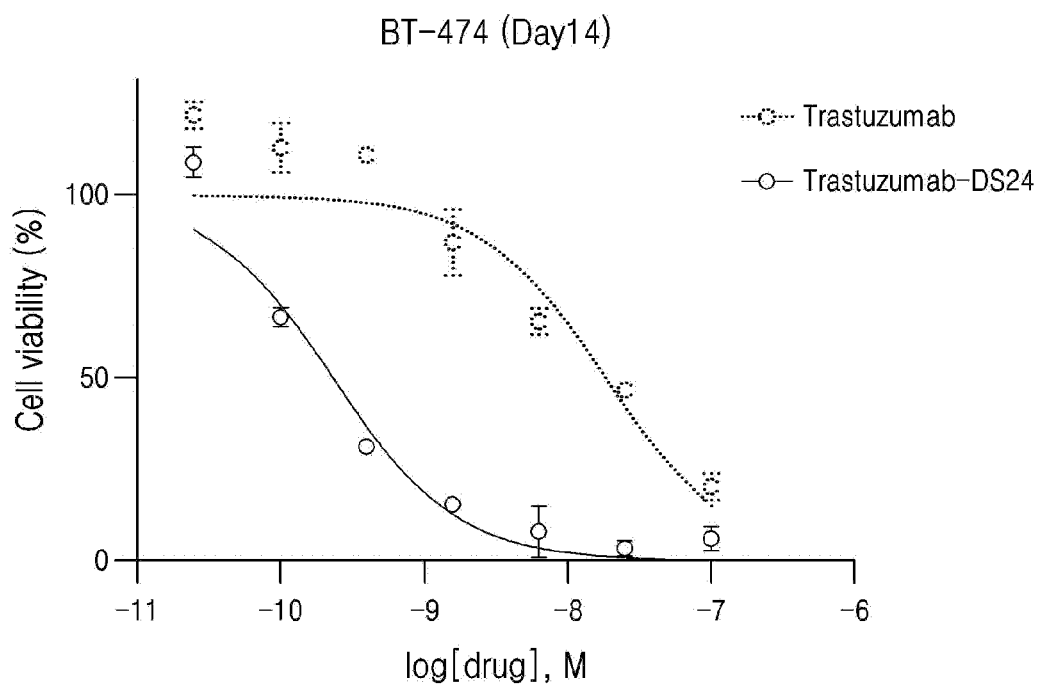

[Fig. 8c]
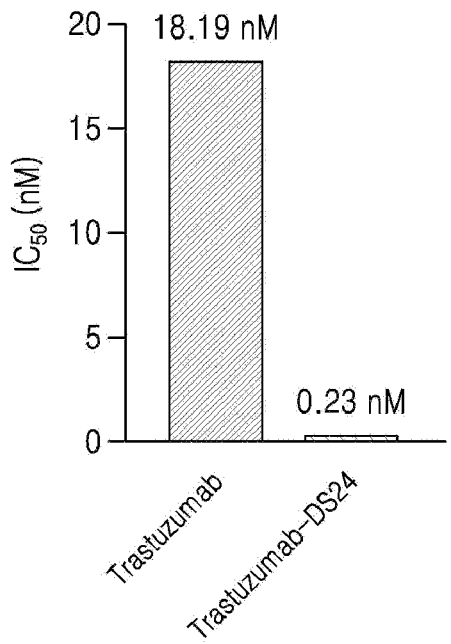
[Fig. 9a]
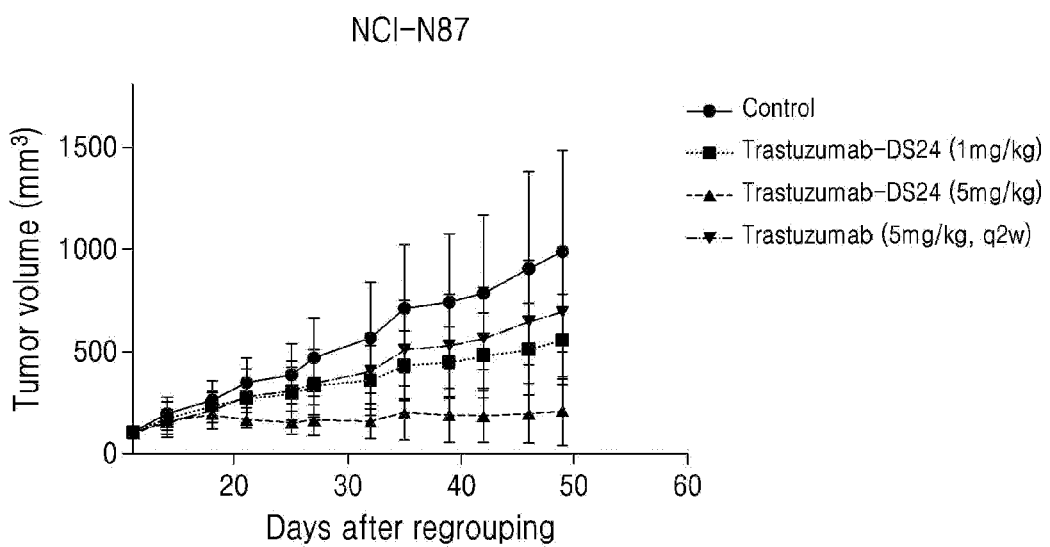

[Fig. 9b]
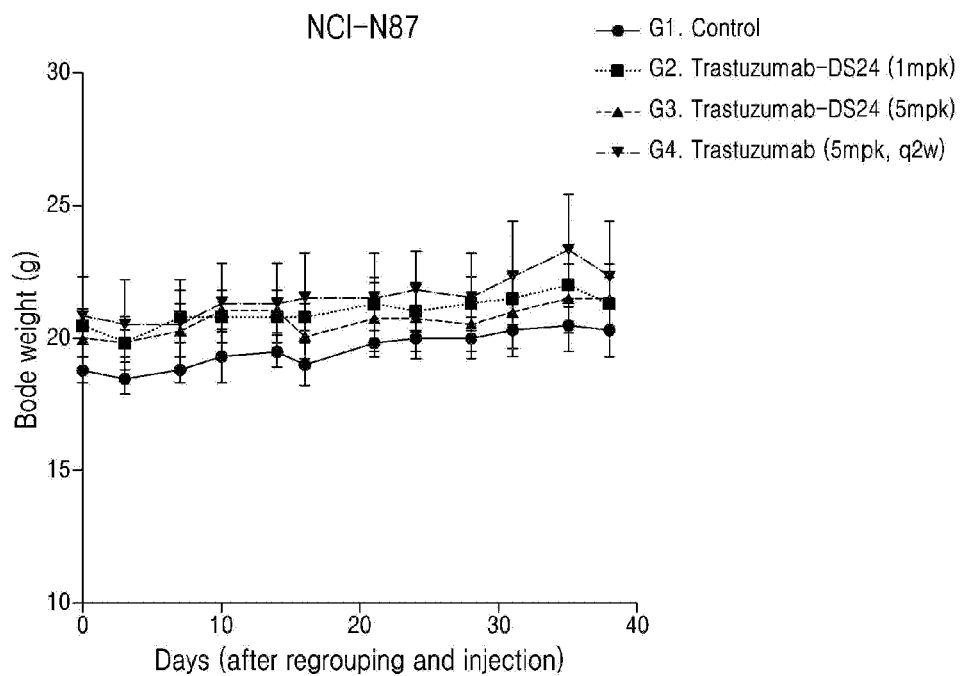
[Fig. 10a]
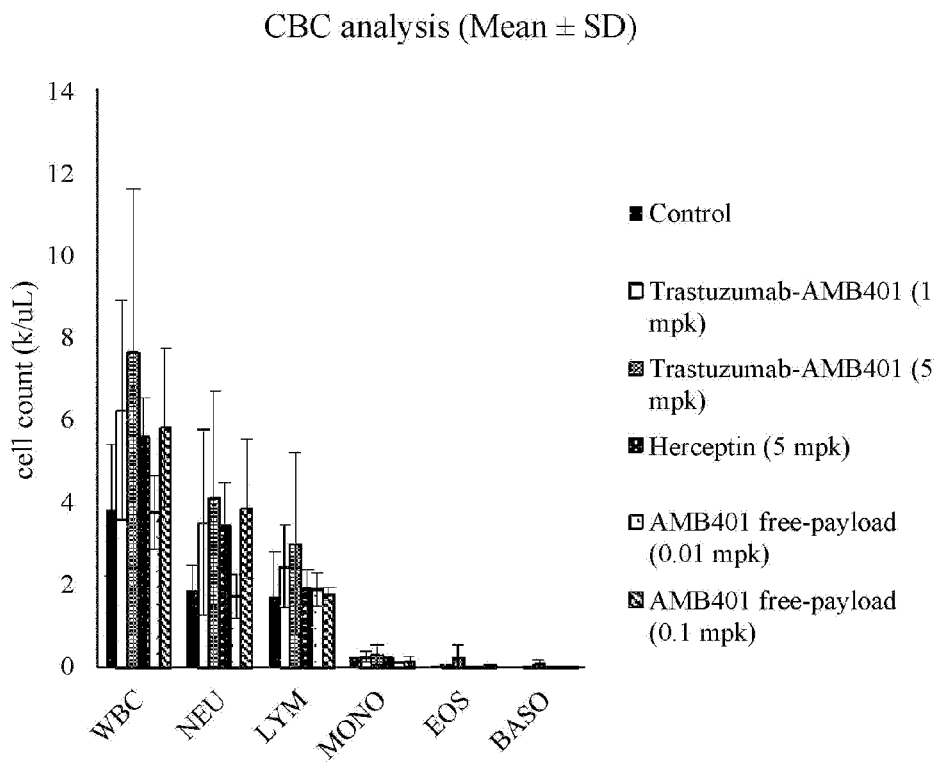

[Fig. 10b i ]
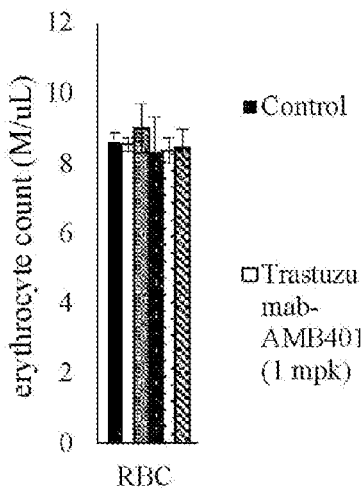
[Fig. 10b ii]
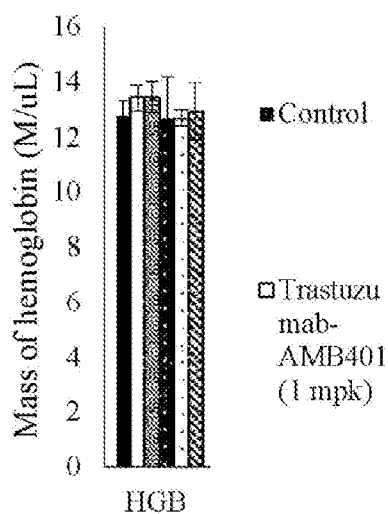

[Fig. 10biii]
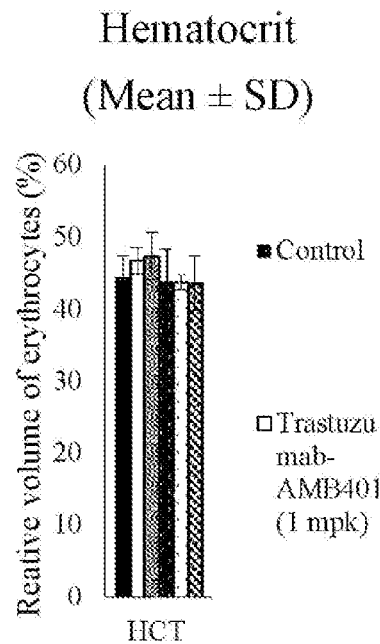
[Fig. 10biv]
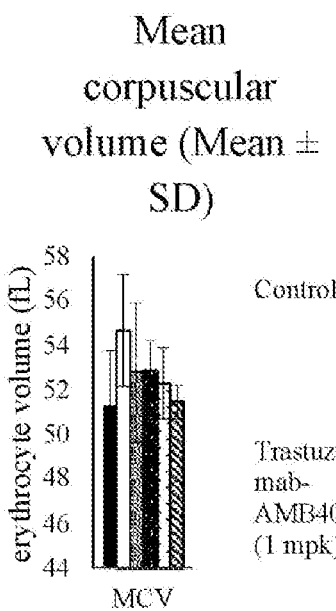

[Fig. 10b v]
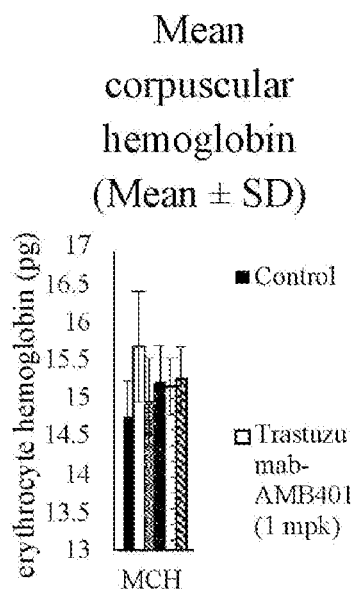
[Fig. 10b vi]
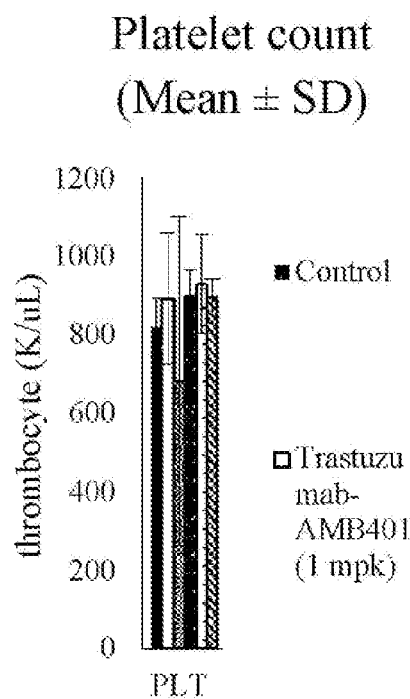

[Fig. 11a]
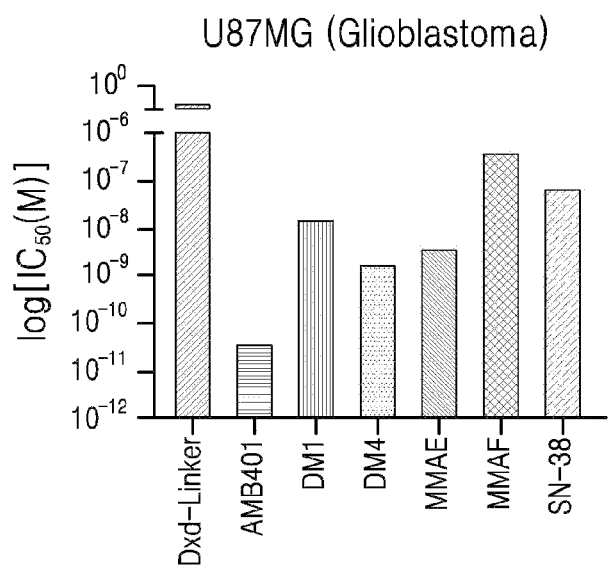
[Fig. 11b]
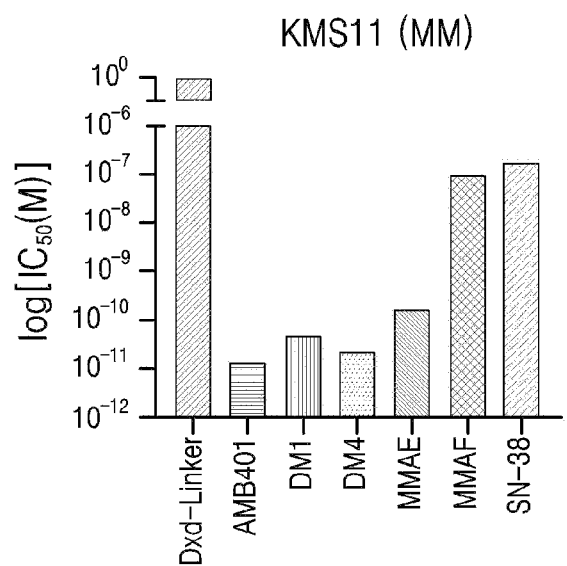

[Fig. 11c]
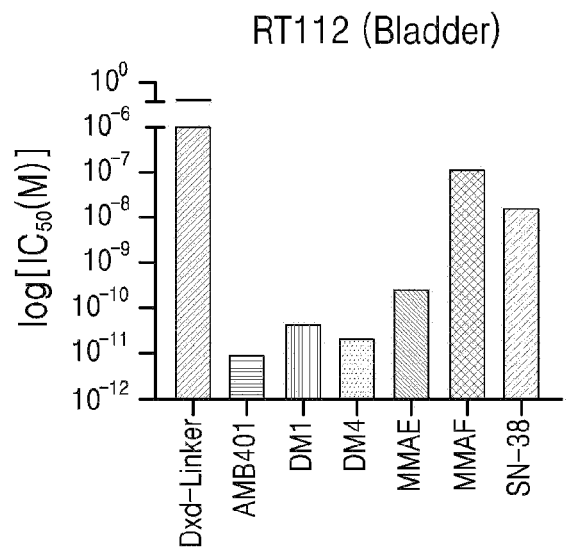
[Fig. 12a]
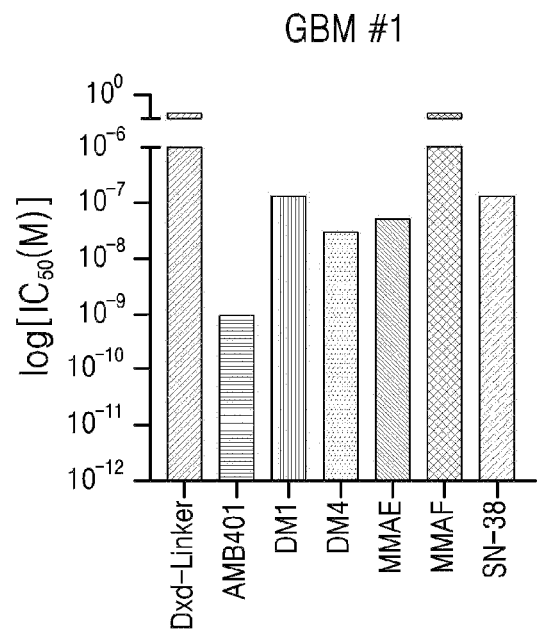

[Fig. 12b]
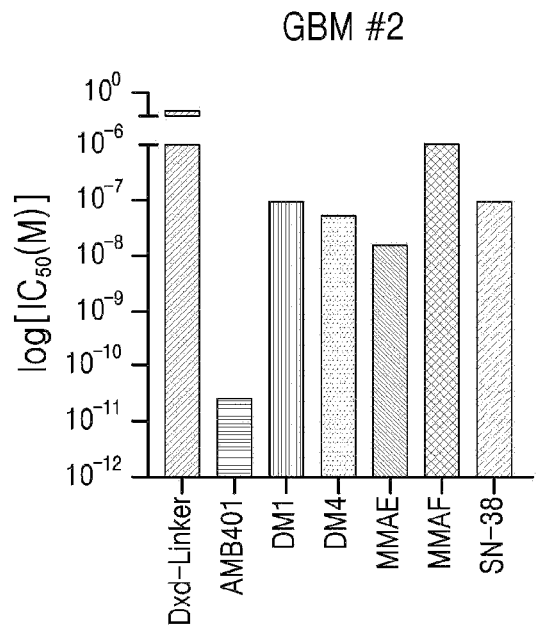
[Fig. 12c]
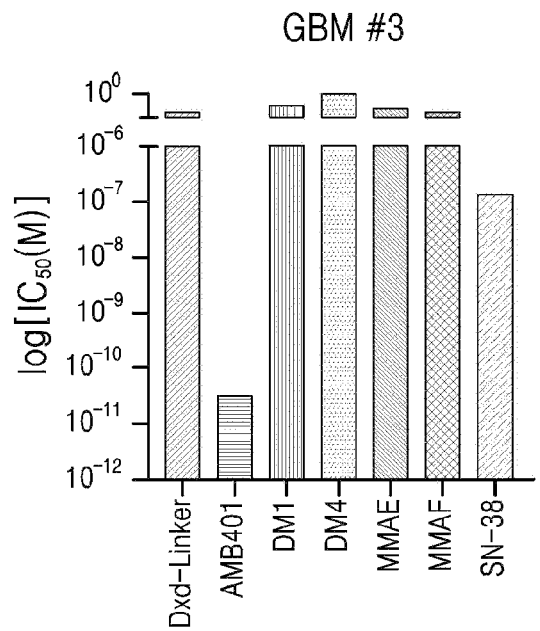

[Fig. 12d]
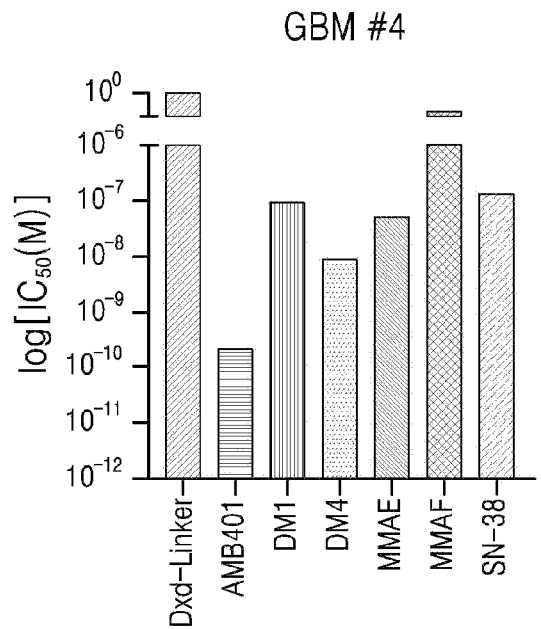
[Fig. 12e]
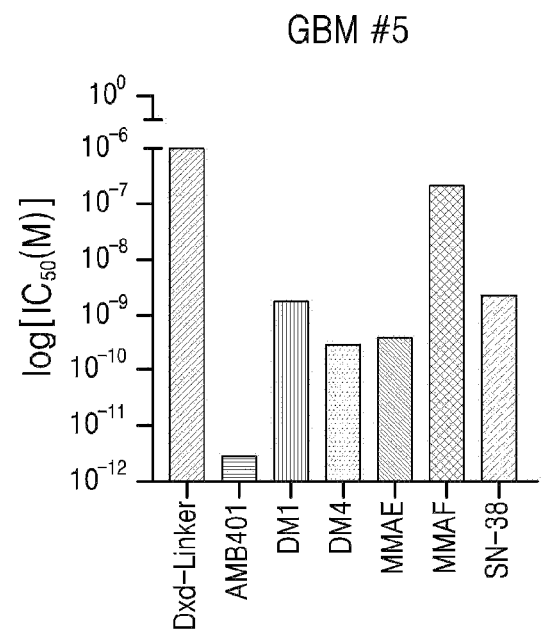

[Fig. 12f]
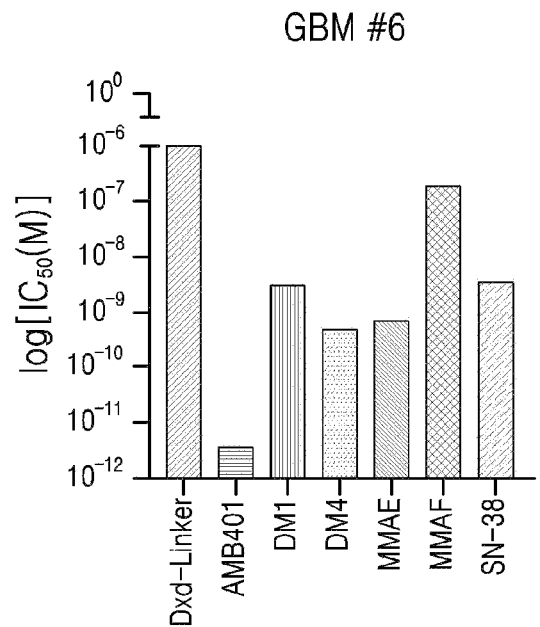
[Fig. 13a]
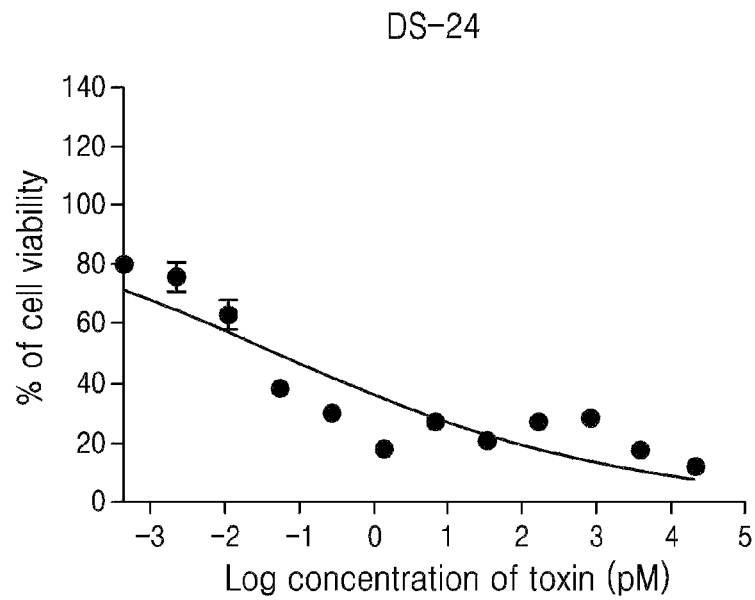

[Fig. 13b]
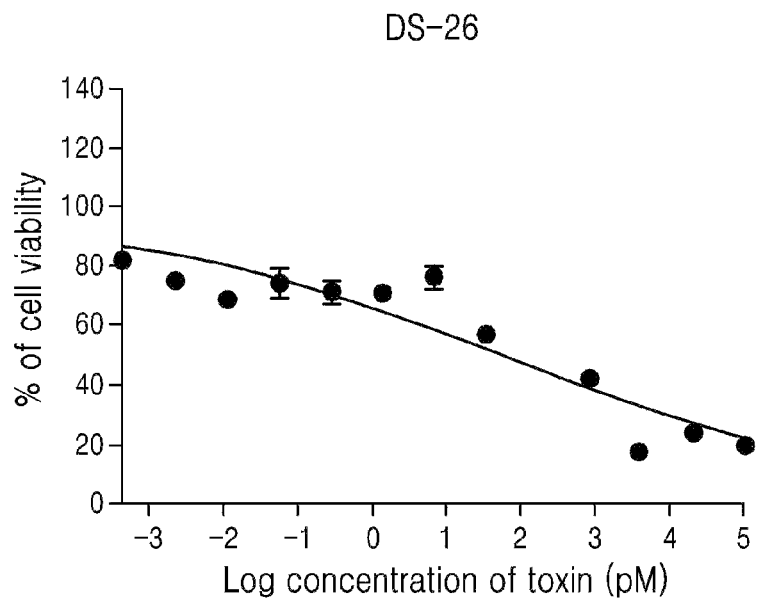
[Fig. 14a]
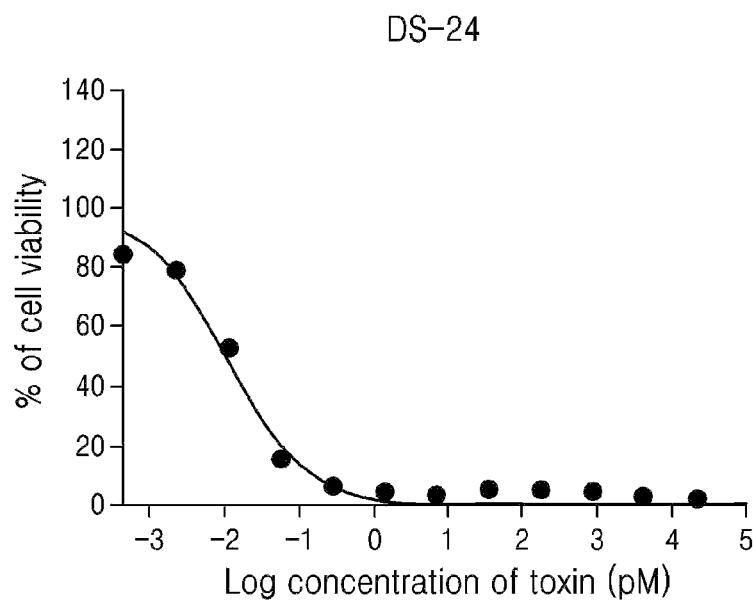

[Fig. 14b]
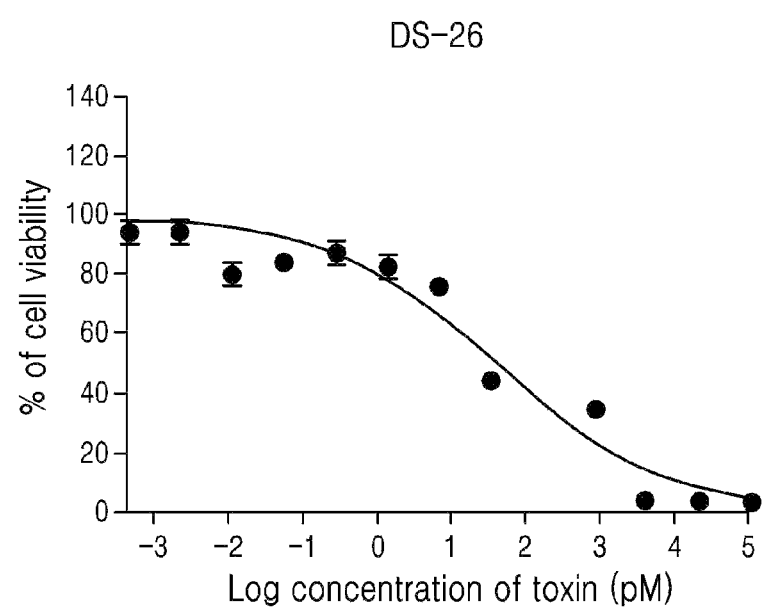

BENZOSELENOPHENE-BASED COMPOUND, PHARMACEUTICAL COMPOSITION CONTAINING SAME, AND ANTIBODY-DRUG CONJUGATE

CROSS-REFERENCE TO RELATED APPLICATIONS

This application is a continuation of PCT Application No. PCT/KR2021/001082, filed on Jan. 27, 2021, which claims priority to Korean Patent Application Number 10-2020-0011222, filed on Jan. 30, 2020, both of which are hereby incorporated by reference in their entirety.

TECHNICAL FIELD

The present disclosure relates to a benzoselenophene-based compound, a method of preparing the benzoselenophene-based compound, and a pharmaceutical composition and antibody-drug conjugate including the benzoselenophene-based compound.

BACKGROUND

Duocarmycin is known as a highly potent anticancer agent. However, duocarmycin may act as a toxin to normal cells and kill an experimental animal in the course of animal experiments. Therefore, duocarmycin itself cannot be used in humans. In this regard, studies to kill only tumor cells by tumor cell-specific response and maintain stability and high activity in blood have been actively conducted.

Antibody therapy has been used to target and treat patients with cancer, immunological disorders and angiogenic disorders. When an antibody-drug conjugate (ADC), i.e., an immunoconjugate, is used to topically deliver a drug, such as a cytotoxic agent or a cell proliferation inhibitor, that kills or suppresses tumor cells in the course of cancer treatment [References: Payne, G. (2003) Cancer Cell 3: 207-212; Trail et al (2003) Cancer Immunol. Immunother. 52:328-337; Syrigos and Epenetos (1999) Anticancer Research 19: 605-614; Niculescu-Duvaz and Springer (1997) Adv. Drug Del. Rev. 26: 151-172; U.S. Pat. No. 4,975,278], it is theoretically possible to perform targeted delivery of the drug to the tumor cells and allows the drug to accumulate within the tumor cells.

However, conventional derivatives having excellent activity are limited in water solubility and thus may aggregate when bound to a target-specific protein such as an antibody, which makes it difficult to synthesize a stable antibody-drug conjugate.

DISCLOSURE OF THE INVENTION

Problems to be Solved by the Invention

The present disclosure is conceived to provide a benzoselenophene-based compound, a method of preparing the benzoselenophene-based compound, and a pharmaceutical composition and antibody-drug conjugate including the benzoselenophene-based compound.

Particularly, the present disclosure relates to preparation of a novel benzoselenophene derivative that is highly increased in water solubility and activity by introducing a novel water-soluble group to benzoselenophene and use of the benzoselenophene derivative as an anticancer drug. The novel water-soluble benzoselenophene derivative of the present disclosure can be used as an antibody-drug conjugate and can function as a prodrug. Also, the water-soluble benzoselenophene derivative can be fused to target-specific substances, such as a protein, a ligand, a nanoparticle and an aptamer, which makes it possible to function as a prodrug.

However, problems to be solved by the present disclosure are not limited to the above-described problems. Although not described herein, other problems to be solved by the present disclosure can be clearly understood by those skilled in the art from the following description.

Means for Solving the Problems

According to a first aspect of the present disclosure, there is provided a benzoselenophene-based compound, represented by the following Chemical Formula 1:

[Chemical Formula 1]

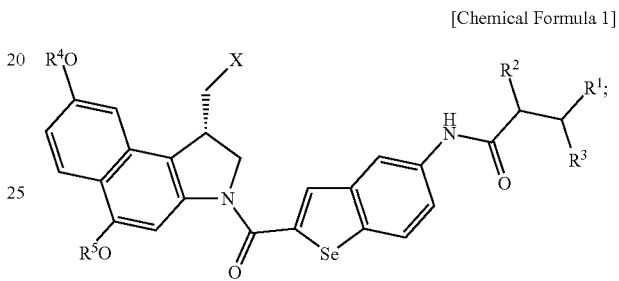

in the above Chemical Formula 1,
$R^1$ is a substituted or unsubstituted $C_{3-10}$ heterocycloalkyl group, a substituted or unsubstituted $C_{5-10}$ aryl group, or a substituted or unsubstituted $C_{3-10}$ heteroaryl group,
each of $R^2$ and $R^3$ is independently hydrogen, fluorine, chlorine, bromine, iodine, or a substituted or unsubstituted $C_{1-5}$ alkyl group,
each of $R^4$ and $R^5$ is independently hydrogen, or a substituted or unsubstituted $C_{1-5}$ alkyl group,
the heterocycloalkyl group and the heteroaryl group include at least one hetero atom selected from N, O and S, and
X is halogen.

According to a second aspect of the present disclosure, there is provided a method of preparing a benzoselenophene-based compound, including: (a) reacting a carboxylic acid represented by the following Chemical Formula 2 with an amine represented by the following Chemical Formula 3 to prepare an intermediate product; and (b) reacting the intermediate product with an amine represented by the following Chemical Formula 4 to obtain a benzoselenophene-based compound represented by the following Chemical Formula 1:

[Chemical Formula 1]

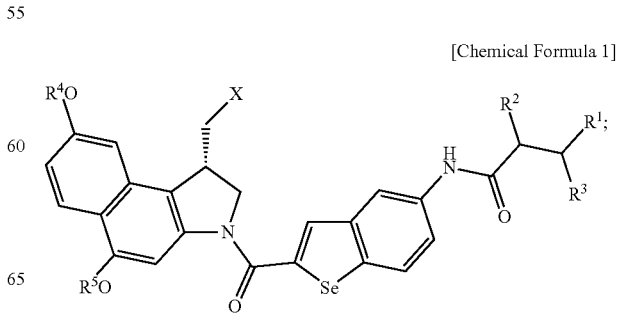

-continued

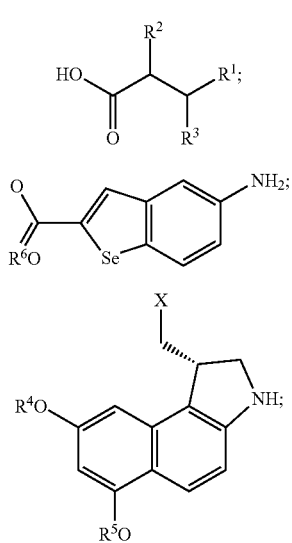

[Chemical Formula 2]

[Chemical Formula 3]

[Chemical Formula 4]

in the above Chemical Formula 1, Chemical Formula 2, Chemical Formula 3 and Chemical Formula 4, $R^1$ is a substituted or unsubstituted $C_{3-10}$ heterocycloalkyl group, a substituted or unsubstituted $C_{5-10}$ aryl group, or a substituted or unsubstituted $C_{3-10}$ heteroaryl group, each of $R^2$ and $R^3$ is independently hydrogen, fluorine, chlorine, bromine, iodine, or a substituted or unsubstituted $C_{1-5}$ alkyl group, each of $R^4$ and $R^5$ is independently hydrogen, or a substituted or unsubstituted $C_{1-5}$ alkyl group, $R^6$ is a substituted or unsubstituted $C_{1-5}$ alkyl group, the heterocycloalkyl group and the heteroaryl group include at least one hetero atom selected from N, O and S, and X is halogen.

According to a third aspect of the present disclosure, there is provided a pharmaceutical composition, including a benzoselenophene-based compound represented by the following Chemical Formula 1 or a pharmaceutically acceptable salt thereof, and the pharmaceutical composition is for preventing or treating proliferative diseases:

[Chemical Formula 1]

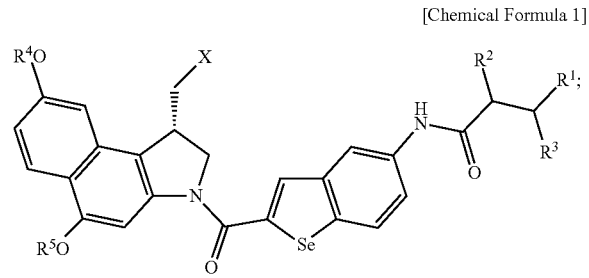

in the above Chemical Formula 1, $R^1$ is a substituted or unsubstituted $C_{3-10}$ heterocycloalkyl group, a substituted or unsubstituted $C_{5-10}$ aryl group, or a substituted or unsubstituted $C_{3-10}$ heteroaryl group, each of $R^2$ and $R^3$ is independently hydrogen, fluorine, chlorine, bromine, iodine, or a substituted or unsubstituted $C_{1-5}$ alkyl group, each of $R^4$ and $R^5$ is independently hydrogen, or a substituted or unsubstituted $C_{1-5}$ alkyl group, the heterocycloalkyl group and the heteroaryl group include at least one hetero atom selected from N, O and S, and X is halogen.

According to a fourth aspect of the present disclosure, there is provided an antibody-drug conjugate or a pharmaceutically acceptable salt thereof, including an antibody; a linker; and a benzoselenophene-based compound represented by the following Chemical Formula 1 or a pharmaceutically acceptable salt thereof:

[Chemical Formula 1]

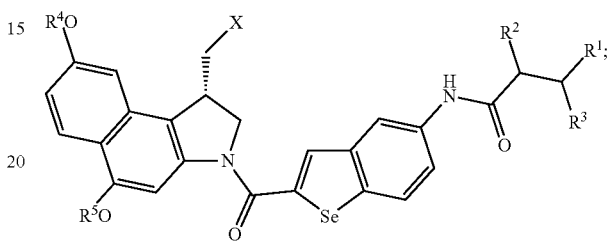

in the above Chemical Formula 1, $R^1$ is a substituted or unsubstituted $C_{3-10}$ heterocycloalkyl group, a substituted or unsubstituted $C_{5-10}$ aryl group, or a substituted or unsubstituted $C_{3-10}$ heteroaryl group, each of $R^2$ and $R^3$ is independently hydrogen, fluorine, chlorine, bromine, iodine, or a substituted or unsubstituted $C_{1-5}$ alkyl group, each of $R^4$ and $R^5$ is independently hydrogen, or a substituted or unsubstituted $C_{1-5}$ alkyl group, the heterocycloalkyl group and the heteroaryl group include at least one hetero atom selected from N, O and S, and X is halogen.

According to a fifth aspect of the present disclosure, there is provided an anticancer composition including the antibody-drug conjugate or the pharmaceutically acceptable salt thereof according to the fourth aspect.

Effects of the Invention

According to the embodiments of the present disclosure, it is possible to prepare a novel benzoselenophene derivative that is highly increased in water solubility and activity by introducing a novel water-soluble group, and the benzoselenophene derivative can be used as an anticancer drug. The novel water-soluble benzoselenophene derivative of the present disclosure can be used as an antibody-drug conjugate and can function as a prodrug. Also, the water-soluble benzoselenophene derivative can be fused to target-specific substances, such as a protein, a ligand, a nanoparticle and an aptamer, which makes it possible to function as a prodrug.

According to the embodiments of the present disclosure, benzoselenophene-based compounds are substances having highly potent anticancer effect with $IC_{50}$ to cancer cells in the range of nM or pM and can be applied to the development of new drugs using antibody-drug conjugates.

A benzoselenophene-based compound, and a pharmaceutical composition and antibody-drug conjugate including the same according to the embodiments of the present disclosure have a remarkable therapeutic effect on cancer, and have excellent anticancer and therapeutic effects particularly on brain cancer, brain metastasis, non-small cell lung cancer and melanoma.

According to the embodiments of the present disclosure, it is possible to synthesize a DNA alkylating derivative containing a benzoselenophene-based compound excellent in water solubility and activity and apply the DNA alkylating derivative as an anticancer drug or a precursor thereof.

A benzoselenophene compound derivative according to the embodiments of the present disclosure can be bound to an antibody-drug conjugate or a protein-conjugate to act on a target in a target-directed manner and thus can have a selective effect through specific treatment.

A benzoselenophene derivative (precursor, prodrug), a benzoselenophene derivative-linker and a benzoselenophene derivative-linker-ligand conjugate according to the embodiments of the present disclosure themselves are stable, but can be used for targeting proliferative diseases such as cancer (particularly, brain cancer, brain metastasis, melanoma, non-small cell lung cancer), specific treatment and/or maximizing medicinal effect. Therefore, they have industrial applicability.

BRIEF DESCRIPTION OF THE DRAWINGS

FIG. 1 shows the SEC analysis results of trastuzumab-glucuronide-Compound 3 ADC prepared according to an example of the present disclosure.

FIG. 2 shows the HIC analysis results of trastuzumab-glucuronide-Compound 3 ADC prepared according to an example of the present disclosure.

FIG. 3 shows the PLRP analysis results of trastuzumab-glucuronide-Compound 3 ADC prepared according to an example of the present disclosure.

FIG. 4 is a table showing the analysis results of in vitro cell line activity of Compound 3 prepared according to an example of the present disclosure.

FIGS. 5A to 5C show respectively graphs about analysis on in vivo cell line activity of Compound 3 (DS-24) prepared according to an example of the present disclosure. FIGS. 5A and 5B show Tumor volume with respect to dosage of DS-24 on Day 0 and Day 6, respectively, and FIG. 5C shows Tumor volume with respect to dosage and date of administration.

FIG. 6 shows the analysis results of correlation of Compound 3 prepared according to an example of the present disclosure with respective cancer types in NCI cell lines.

FIG. 7A is a graph showing nonlinear regression analysis of the dose-response curve for cell viability of MCF-7 and NCI-N87 cells treated with ADC (DS-24), and FIG. 7B shows data of $IC_{50}$ values as a result thereof.

FIG. 8A is the setup for confirming the effect of ADC (DS-24) on inhibiting a BT474 tumor spheroid, FIG. 8B is a graph showing nonlinear regression analysis of the dose-response curve, and FIG. 8C shows data of $IC_{50}$ values as a result thereof.

FIG. 9A and FIG. 9B show data on the anticancer effect of ADC (DS-24) in NCI-N87 xenograft animal models and changes in body weight of nude mice administered with ADC (DS-24), respectively.

FIG. 10A, and FIGS. 10B i to 10Bvi show inflammatory cell counts and anemia-associated values, respectively, according to toxicity analysis through a complete blood count (CBC) test of ADC (DS-24) in NCI-N87 xenograft animal models.

FIG. 11A, FIG. 11B and FIG. 11C show data confirming the cell viability inhibitory effect of seven types of payloads except Compound 3 (DS-24) on the glioblastoma cell line U87MG, the multiple myeloma cell line KMS11, and the bladder cancer cell line RT112, respectively.

FIG. 12A, FIG. 12B, FIG. 12C, FIG. 12D, FIG. 12E and FIG. 12F show data confirming the cell viability inhibitory effect of seven types of payloads except Compound 3 (DS-24) on 6 types of cells derived from a patient with glioblastoma, respectively.

FIG. 13A and FIG. 13B are graphs showing the cell viability of NCI-N87 depending on the concentrations of DS-24 and DS-26, respectively.

FIG. 14A and FIG. 14B are graphs showing the cell viability of SK-OV3 depending on the concentrations of DS-24 and DS-26, respectively.

BEST MODE FOR CARRYING OUT THE INVENTION

Hereinafter, examples of the present disclosure will be described in detail with reference to the accompanying drawings so that the present disclosure may be readily implemented by those skilled in the art. However, it is to be noted that the present disclosure is not limited to the examples but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element.

Through the whole document, the term "on" that is used to designate a position of one element with respect to another element includes both a case that the one element is adjacent to the other element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party.

Through the whole document, the term "step of" does not mean "step for".

Through the whole document, the term "combination(s) of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, a phrase in the form "A and/or B" means "A or B, or A and B".

Through the whole document, the term "alkyl" includes linear or branched alkyl groups having 1 to 12 carbon atoms, 1 to 10 carbon atoms, 1 to 8 carbon atoms, 1 to 5 carbon atoms, or 1 to 4 carbon atoms and all the possible isomers thereof. For example, the alkyl group may include methyl group (Me), ethyl group (Et), n-propyl group ("Pr), isopropyl group (ⁱPr), n-butyl group (ⁿBu), tert-butyl group (ᵗBu), iso-butyl group (ⁱBu), sec-butyl group (ˢBu), pentyl group, hexyl group, iso-hexyl group, heptyl group, 4,4-dimethyl pentyl group, octyl group, 2,2,4-trimethyl pentyl group, nonyl group, decyl group, undecyl group, dodecyl group, and isomers thereof, but may not be limited thereto.

In the following description, exemplary embodiments of the present disclosure will be described in detail, but the present disclosure may not be limited thereto.

According to a first aspect of the present disclosure, there is provided a benzoselenophene-based compound, represented by the following Chemical Formula 1:

[Chemical Formula 1]

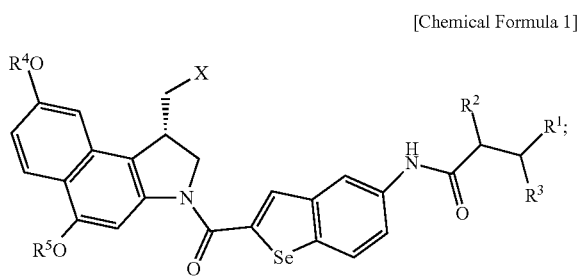

in the above Chemical Formula 1, $R^1$ is a substituted or unsubstituted $C_{3-10}$ heterocycloalkyl group, a substituted or unsubstituted $C_{5-10}$ aryl group, or a substituted or unsubstituted $C_{3-10}$ heteroaryl group, each of $R^2$ and $R^3$ is independently hydrogen, fluorine, chlorine, bromine, iodine, or a substituted or unsubstituted $C_{1-5}$ alkyl group, each of $R^4$ and $R^5$ is independently hydrogen, or a substituted or unsubstituted $C_{1-5}$ alkyl group, the heterocycloalkyl group and the heteroaryl group include at least one hetero atom selected from N, O and S, and X is halogen.

In an embodiment of the present disclosure, if the functional groups are substituted, the substituents may include one or more members selected from an acyl group, an amino group (including amino group, mono- and dialkylamino groups, mono- and diarylamino groups and an alkylarylamino group), an acylamino group (including carbamoyl and ureido group), an alkylcarbonyloxy group, an arylcarbonyloxy group, an alkoxycarbonyloxy group, an alkoxycarbonyl group, a carboxy group, carboxylate group, an aminocarbonyl group, mono- and dialkylaminocarbonyl groups, cyano group, azido group, a halogen group, hydroxyl group, nitro group, trifluoromethyl group, thiol group, an alkylthiol group, an arylthiol group, an alkylthiocarbonyl group, a thiocarboxylate group, a lower alkyl group, a lower alkenyl group, a lower alkynyl group, a cycloalkyl group, a heterocycloalkyl group, an aryl group, a heteroaryl group, a lower alkoxy group, an aryloxy group, an aryloxycarbonyloxy group, a benzyloxy group, a benzyl group, a sulfinyl group, an alkylsulfinyl group, a sulfonyl group, a sulfate group, a sulfonate group, a sulfonamide group, a phosphate group, a phosphonate group, a phosphinato group, an oxo group, a guanidine group, imino group and formyl group, but may not be limited thereto.

In an embodiment of the present disclosure, $R^1$ may include a $C_{3-10}$ heterocycloalkyl group or a $C_{3-10}$ heteroaryl group including at least one nitrogen atom, and each of $R^4$ and $R^5$ may be independently hydrogen, methyl group or ethyl group, but may not be limited thereto.

In an embodiment of the present disclosure, X may be F, Cl, Br or I, but may not be limited thereto. Further, in an embodiment of the present disclosure, X may be Cl.

In an embodiment of the present disclosure, a benzoselenophene-based compound of the present disclosure contains two sp³ carbon atoms as a main framework in —CHR²CHR¹R³, linked to a benzoselenophene host by an amide bond, and thus, the flexibility of the molecule itself can be increased. Further, desirably, $R^1$ may contain various derivatives of a pentagonal or hexagonal ring including N, O or S. In addition, $R^1$ may contain a bicyclic ring with or without a hetero atom, which may facilitate minor groove binding of DNA in an anticancer mechanism.

In an embodiment of the present disclosure, $R^1$ may include pyrrolidinyl group (—NC₄H₈), piperidinyl group (—NC₅H₁₀), piperazinyl group (—N₂C₄H₉), 4-methylpiperazin-1-yl group (—N₂C₅H₁₁), morpholino group (—NOC₄H₈),

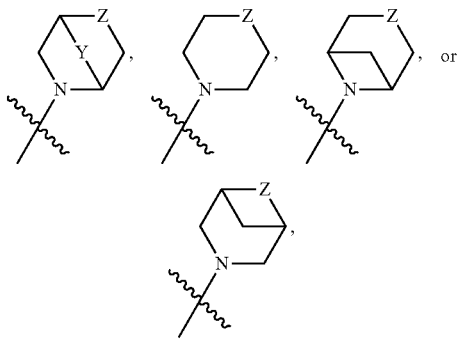

Y may include —CH₂— or —C₂H₄—, Z may include —CHR—, —NR, —O—, or —S—, and R may include hydrogen or a $C_{1-3}$ alkyl group, but may not be limited thereto.

In an embodiment of the present disclosure, $R^1$ may be pyrrolidinyl group (—NC₄H₈), piperidinyl group (—NC₅H₁₀), piperazinyl group (—N₂C₄H₉), 4-methylpiperazin-1-yl group (—N₂C₅H₁₁), or morpholino group (—NOC₄H₈).

In an embodiment of the present disclosure, both $R^2$ and $R^3$ may be hydrogen.

In an embodiment of the present disclosure, each of $R^5$ and $R^6$ may be independently hydrogen, methyl group, ethyl group or a propyl group.

In an embodiment of the present disclosure, the benzoselenophene-based compound may include the following:

[Compound 3]

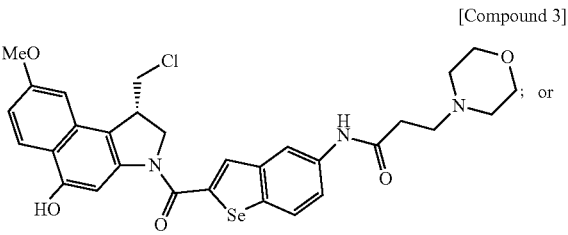

; or

-continued

[Compound 4]

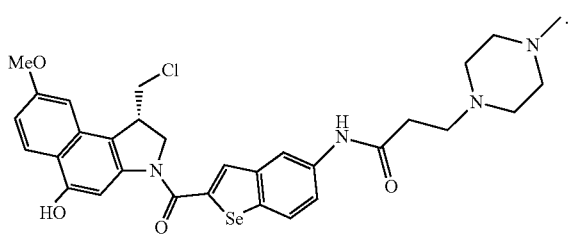

According to a second aspect of the present disclosure, there is provided a method of preparing a benzoselenophene-based compound, including: (a) reacting a carboxylic acid represented by the following Chemical Formula 2 with an amine represented by the following Chemical Formula 3 to prepare an intermediate product; and (b) reacting the intermediate product with an amine represented by the following Chemical Formula 4 to obtain a benzoselenophene-based compound represented by the following Chemical Formula 1:

[Chemical Formula 1]

[Chemical Formula 2]

[Chemical Formula 3]

[Chemical Formula 4]

in the above Chemical Formula 1, Chemical Formula 2, Chemical Formula 3 and Chemical Formula 4, $R^1$ is a substituted or unsubstituted $C_{3-10}$ heterocycloalkyl group, a substituted or unsubstituted $C_{5-10}$ aryl group, or a substituted or unsubstituted $C_{3-10}$ heteroaryl group, each of $R^2$ and $R^3$ is independently hydrogen, fluorine, chlorine, bromine, iodine, or a substituted or unsubstituted $C_{1-5}$ alkyl group, each of $R^4$ and $R^5$ is independently hydrogen, or a substituted or unsubstituted $C_{1-5}$ alkyl group, $R^6$ is a substituted or unsubstituted $C_{1-5}$ alkyl group, the heterocycloalkyl group and the heteroaryl group include at least one hetero atom selected from N, O and S, and X is halogen.

Detailed descriptions on the second aspect of the present disclosure, which overlap with those on the first aspect of the present disclosure, are omitted hereinafter, but the descriptions of the first aspect of the present disclosure may be identically applied to the second aspect of the present disclosure, even though they are omitted hereinafter.

In an embodiment of the present disclosure, if the functional groups are substituted, the substituents may include one or more members selected from an acyl group, an amino group (including amino group, mono- and dialkylamino groups, mono- and diarylamino groups and an alkylarylamino group), an acylamino group (including carbamoyl and ureido group), an alkylcarbonyloxy group, an arylcarbonyloxy group, an alkoxycarbonyloxy group, an alkoxycarbonyl group, a carboxy group, carboxylate group, an aminocarbonyl group, mono- and dialkylaminocarbonyl groups, cyano group, azido group, a halogen group, hydroxyl group, nitro group, trifluoromethyl group, thiol group, an alkylthiol group, an arylthiol group, an alkylthiocarbonyl group, a thiocarboxylate group, a lower alkyl group, a lower alkenyl group, a lower alkynyl group, a cycloalkyl group, a heterocycloalkyl group, an aryl group, a heteroaryl group, a lower alkoxy group, an aryloxy group, an aryloxycarbonyloxy group, a benzyloxy group, a benzyl group, a sulfinyl group, an alkylsulfinyl group, a sulfonyl group, a sulfate group, a sulfonate group, a sulfonamide group, a phosphate group, a phosphonate group, a phosphinato group, an oxo group, a guanidine group, imino group and formyl group, but may not be limited thereto.

In an embodiment of the present disclosure, $R^1$ may include a $C_{3-10}$ heterocycloalkyl group or a $C_{3-10}$ heteroaryl group including at least one nitrogen atom, and each of $R^4$ and $R^5$ may be independently hydrogen, methyl group or ethyl group, but may not be limited thereto.

In an embodiment of the present disclosure, X may be F, Cl, Br or I, but may not be limited thereto. Further, in an embodiment of the present disclosure, X may be Cl.

In an embodiment of the present disclosure, a benzoselenophene-based compound of the present disclosure contains two sp$^3$ carbon atoms as a main framework in —CHR$^2$CHR$^1$R$^3$, linked to a benzoselenophene host by an amide bond, and thus, the flexibility of the molecule itself can be increased. Further, desirably, $R^1$ may contain various derivatives of a pentagonal or hexagonal ring including N, O or S. In addition, $R^1$ may contain a bicyclic ring with or without a hetero atom, which may facilitate minor groove binding of DNA in an anticancer mechanism.

In an embodiment of the present disclosure, $R^1$ may include pyrrolidinyl group (—NC$_4$H$_8$), piperidinyl group (—NC$_5$H$_{10}$), piperazinyl group (—N$_2$C$_4$H$_9$), 4-methylpiperazin-1-yl group (—N$_2$C$_5$H$_{11}$), morpholino group (—NOC$_4$H$_8$),

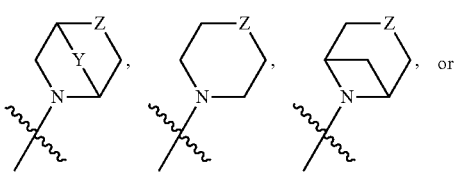

-continued

Y may include —CH$_2$— or —C$_2$H$_4$—, Z may include —CHR—, —NR, —O—, or —S—, and R may include hydrogen or a C$_{1-3}$ alkyl group, but may not be limited thereto.

In an embodiment of the present disclosure, R$^1$ may be pyrrolidinyl group (—NC$_4$H$_8$), piperidinyl group (—NC$_5$H$_{10}$), piperazinyl group (—N$_2$C$_4$H$_9$), 4-methylpiperazin-1-yl group (—N$_2$C$_5$H$_{11}$), or morpholino group (—NOC$_4$H$_8$).

In an embodiment of the present disclosure, both R$^2$ and R$^3$ may be hydrogen.

In an embodiment of the present disclosure, each of R$^5$ and R$^6$ may be independently hydrogen, methyl group, ethyl group or a propyl group.

In an embodiment of the present disclosure, an intermediate product produced from (a) may be in a carboxylic acid form or a carboxylate salt form since R$^6$ is substituted with hydrogen by adjusting a pH, but may not be limited thereto.

In an embodiment of the present disclosure, an amine compound represented by the above Chemical Formula 4 may be obtained by performing an acid treatment on conventionally known seco-MCBI as represented below, but may not be limited thereto:

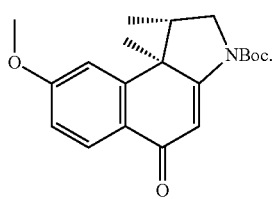 [SMILES: COc1ccc2c(c1)[C@]1(C)C(=CC2=O)N(C(=O)OC(C)(C)C)C[C@H]1C]

In an embodiment of the present disclosure, the benzoselenophene-based compound may include the following:

[00133] [Compound 3]

[00134]

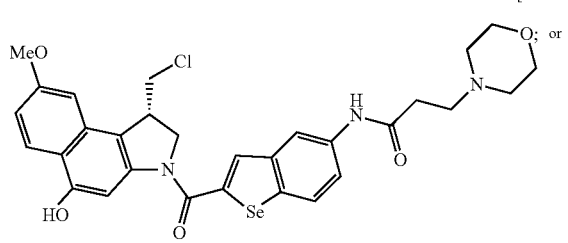

[00135] [Compound 4]

[00136]

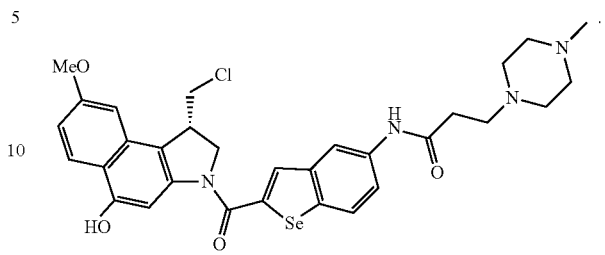

According to a third aspect of the present disclosure, there is provided a pharmaceutical composition, including a benzoselenophene-based compound represented by the following Chemical Formula 1 or a pharmaceutically acceptable salt thereof, and the pharmaceutical composition is for preventing or treating proliferative diseases:

[0138] [Chemical Formula 1]

[00139]

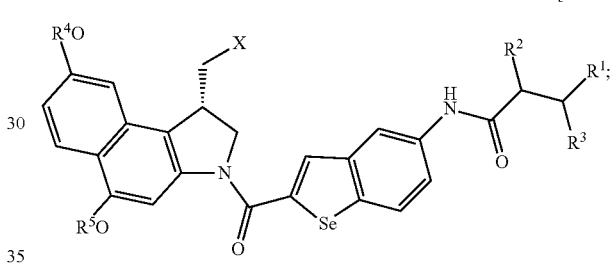

in the above Chemical Formula 1,
R$^1$ is a substituted or unsubstituted C$_{3-10}$ heterocycloalkyl group, a substituted or unsubstituted C$_{5-10}$ aryl group, or a substituted or unsubstituted C$_{3-10}$ heteroaryl group,
each of R$^2$ and R$^3$ is independently hydrogen, fluorine, chlorine, bromine, iodine, or a substituted or unsubstituted C$_{1-5}$ alkyl group,
each of R$^4$ and R$^5$ is independently hydrogen, or a substituted or unsubstituted C$_{1-5}$ alkyl group,
the heterocycloalkyl group and the heteroaryl group include at least one hetero atom selected from N, O and S, and
X is halogen.

Detailed descriptions on the third aspect of the present disclosure, which overlap with those on the first aspect and the second aspect of the present disclosure, are omitted hereinafter, but the descriptions of the first aspect and the second of the present disclosure may be identically applied to the third aspect of the present disclosure, even though they are omitted hereinafter.

In an embodiment of the present disclosure, the benzoselenophene-based compound or the pharmaceutically acceptable salt thereof may be a prodrug, but may not be limited thereto.

In an embodiment of the present disclosure, the benzoselenophene-based compound or the pharmaceutically acceptable salt thereof may be in an active form when present within a solvent or administered into the body, but may not be limited thereto.

In an embodiment of the present disclosure, the proliferative diseases may include at least one selected from neoplasm, tumor, cancer, leukaemia, psoriasis, bone diseases, fibroblastic disorders and atherosclerosis, but may not be limited thereto.

In an embodiment of the present disclosure, the cancer may include at least one selected from solid tumor, hematologic malignancy, calorectal cancer, uterine cancer, uterine myoma, meningioma, lung cancer, small cell lung cancer, non-small cell lung cancer, gastrointestinal malignancy, colorectal cancer, intestinal cancer, breast cancer, ovarian cancer, prostate cancer, testis cancer, liver cancer, renal cancer, bladder cancer, pancreatic cancer, brain cancer, brain metastasis, sarcoma, osteogenic sarcoma, Kaposi sarcoma and melanoma, but may not be limited thereto. A pharmaceutical composition according to an embodiment of the present disclosure can be applied to various diseases, not limited to types of cancer, as targets for prevention or treatment.

In an embodiment of the present disclosure, if the functional groups are substituted, the substituents may include one or more members selected from an acyl group, an amino group (including amino group, mono- and dialkylamino groups, mono- and diarylamino groups and an alkylarylamino group), an acylamino group (including carbamoyl and ureido group), an alkylcarbonyloxy group, an arylcarbonyloxy group, an alkoxycarbonyloxy group, an alkoxycarbonyl group, a carboxy group, carboxylate group, an aminocarbonyl group, mono- and dialkylaminocarbonyl groups, cyano group, azido group, a halogen group, hydroxyl group, nitro group, trifluoromethyl group, thiol group, an alkylthiol group, an arylthiol group, an alkylthiocarbonyl group, a thiocarboxylate group, a lower alkyl group, a lower alkenyl group, a lower alkynyl group, a cycloalkyl group, a heterocycloalkyl group, an aryl group, a heteroaryl group, a lower alkoxy group, an aryloxy group, an aryloxycarbonyloxy group, a benzyloxy group, a benzyl group, a sulfinyl group, an alkylsulfinyl group, a sulfonyl group, a sulfate group, a sulfonate group, a sulfonamide group, a phosphate group, a phosphonate group, a phosphinato group, an oxo group, a guanidine group, imino group and formyl group, but may not be limited thereto.

In an embodiment of the present disclosure, $R^1$ may include a $C_{3-10}$ heterocycloalkyl group or a $C_{3-10}$ heteroaryl group including at least one nitrogen atom, and each of $R^4$ and $R^5$ may be independently hydrogen, methyl group or ethyl group, but may not be limited thereto.

In an embodiment of the present disclosure, X may be F, Cl, Br or I, but may not be limited thereto. Further, in an embodiment of the present disclosure, X may be Cl.

In an embodiment of the present disclosure, a benzoselenophene-based compound of the present disclosure contains two $sp^3$ carbon atoms as a main framework in —$CHR^2CHR^1R^3$, linked to a benzoselenophene host by an amide bond, and thus, the flexibility of the molecule itself can be increased. Further, desirably, $R^1$ may contain various derivatives of a pentagonal or hexagonal ring including N, O or S. In addition, $R^1$ may contain a bicyclic ring with or without a hetero atom, which may facilitate minor groove binding of DNA in an anticancer mechanism.

In an embodiment of the present disclosure, $R^1$ may include pyrrolidinyl group (—$NC_4H_8$), piperidinyl group (—$NC_5H_{10}$), piperazinyl group (—$N_2C_4H_9$), 4-methylpiperazin-1-yl group (—$N_2C_5H_{11}$), morpholino group (—$NOC_4H_8$),

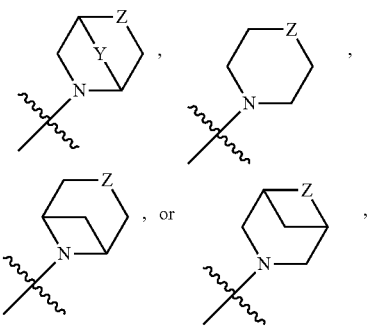

Y may include —$CH_2$— or —$C_2H_4$—, Z may include —CHR—, —NR, —O—, or —S—, and R may include hydrogen or a $C_{1-3}$ alkyl group, but may not be limited thereto.

In an embodiment of the present disclosure, $R^1$ may be pyrrolidinyl group (—$NC_4H_8$), piperidinyl group (—$NC_5H_{10}$), piperazinyl group (—$N_2C_4H_9$), 4-methylpiperazin-1-yl group (—$N_2C_5H_{11}$), or morpholino group (—$NOC_4H_8$).

In an embodiment of the present disclosure, both $R^2$ and $R^3$ may be hydrogen.

In an embodiment of the present disclosure, each of $R^5$ and $R^6$ may be independently hydrogen, methyl group, ethyl group or a propyl group.

In an embodiment of the present disclosure, the benzoselenophene-based compound may include the following:

[Compound 3]

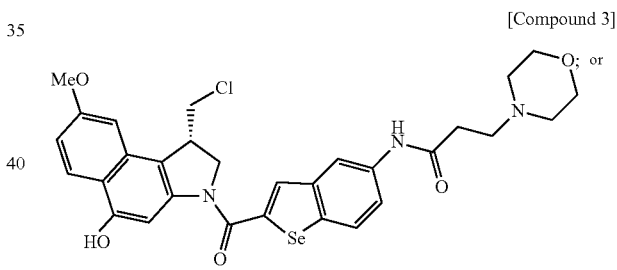

[Compound 4]

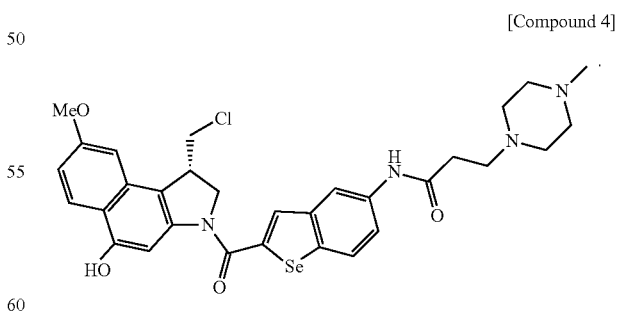

According to a fourth aspect of the present disclosure, there is provided an antibody-drug conjugate or a pharmaceutically acceptable salt thereof, including an antibody; a linker; and a benzoselenophene-based compound represented by the following Chemical Formula 1 or a pharmaceutically acceptable salt thereof:

[Chemical Formula 1]

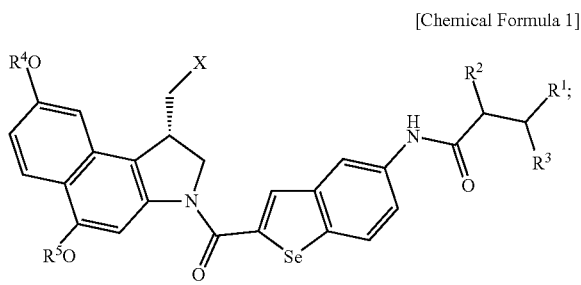

in the above Chemical Formula 1,
$R^1$ is a substituted or unsubstituted $C_{3-10}$ heterocycloalkyl group, a substituted or unsubstituted $C_{5-10}$ aryl group, or a substituted or unsubstituted $C_{3-10}$ heteroaryl group,
each of $R^2$ and $R^3$ is independently hydrogen, fluorine, chlorine, bromine, iodine, or a substituted or unsubstituted $C_{1-5}$ alkyl group,
each of $R^4$ and $R^5$ is independently hydrogen, or a substituted or unsubstituted $C_{1-5}$ alkyl group,
the heterocycloalkyl group and the heteroaryl group include at least one hetero atom selected from N, O and S, and
X is halogen.

Detailed descriptions on the fourth aspect of the present disclosure, which overlap with those on the first aspect to the third aspect of the present disclosure, are omitted hereinafter, but the descriptions of the first aspect to the third of the present disclosure may be identically applied to the third aspect of the present disclosure, even though they are omitted hereinafter.

In an embodiment of the present disclosure, the antibody-drug conjugate or a pharmaceutically acceptable salt thereof may be a prodrug, but may not be limited thereto.

In an embodiment of the present disclosure, the antibody-drug conjugate or a pharmaceutically acceptable salt thereof may be in an active form when present within a solvent or administered into the body, but may not be limited thereto.

In an embodiment of the present disclosure, the antibody may include an antibody, an antibody variant or antigen-biding fragments thereof immunospecific to a proliferative disease, but may not be limited thereto. Here, the term "antibody" may encompass a polyclonal antibody and a monoclonal antibody, and desirably, it may be a monoclonal antibody and may have a whole antibody form. The whole antibody has two full-length light chains and two full-length heavy chains and includes an invariant domain, and each light chain is linked to a heavy chain by a disulfide bond. Also, in an embodiment of the present disclosure, the antibody may include a monoclonal antibody, a multispecific antibody, a human antibody, a humanized antibody, a chimeric antibody, a short chain Fvs (scFV), a short chain antibody, Fab fragments, F(ab') fragments, a disulfide-binding FVs (dsFV) and an anti-idiotype (anti-Id) antibody, or epitope-binding fragments thereof, and the like, but may not be limited thereto. A whole anti-c-Met antibody according to embodiments of the present disclosure encompasses IgA, IgD, IgE, IgM and IgG, and IgG encompasses IgG1, IgG2, IgG3, and IgG4 as subtypes thereof. Further, the term "antibody variant" includes a double antibody, and the double antibody refers to an antibody to a single substance containing antibodies or antibody-binding fragments that recognize different antigens, respectively, and may include an antibody or antigen-binding fragment thereof which is specific to a cancer-related antigen or an immune checkpoint protein antigen or which binds specifically to an immune effector cell-related antigen, but may not be limited to limited antibody frameworks. Further, the term "antigen-binding fragment" refers to a fragment having the ability to specifically bind to the antigen, and may include Fab, Fab', F(ab')2, scFv (scFv)2, scFv-Fc and Fv.

In an embodiment of the present disclosure, the proliferative diseases may include at least one selected from neoplasm, tumor, cancer, leukaemia, psoriasis, bone diseases, fibroblastic disorders and atherosclerosis, but may not be limited thereto.

In an embodiment of the present disclosure, the cancer may include at least one selected from solid tumor, hematologic malignancy, calorectal cancer, uterine cancer, uterine myoma, meningioma, lung cancer, small cell lung cancer, non-small cell lung cancer, gastrointestinal malignancy, colorectal cancer, intestinal cancer, breast cancer, ovarian cancer, prostate cancer, testis cancer, liver cancer, renal cancer, bladder cancer, pancreatic cancer, brain cancer, brain metastasis, sarcoma, osteogenic sarcoma, Kaposi sarcoma and melanoma, but may not be limited thereto. A pharmaceutical composition according to an embodiment of the present disclosure can be applied to various diseases, not limited to types of cancer, as targets for prevention or treatment.

In an embodiment of the present disclosure, the antibody may bind to at least one tumor-related antigens or cell surface acceptors selected from the followings, but may not be limited thereto. Also, the antibody may bind to the following various antigens that are conventionally known, but may not be limited thereto:

(1) BMPR1B (bone morphogenetic protein receptor-type 1B); (2) E16 (LAT1, SLC7A5); (3) STEAP1 (six transmembrane epithelial antigen of prostate); (4) 0772P (CA125, MUC16); (5) MPF (MPF, MSLN, SMR, megakaryocyte potentiating factor, mesothelin); (6) Napi3b [NAPI-3B, NPTIIb, SLC34A2, solute carrier family 34 (sodium phosphate), member 2, type II sodium-dependent phosphate transporter (3b); (7) Sema 5b (FLJ10372, KIAA1445, Mm.42015, SEMA5B, SEMAG, Semaphorin 5b H log, sema domain, seven thrombospondin repeats (type 1 and type 1-like), transmembrane domain (TM) and short cytoplasmic domain, (semaphorin) 5B); (8) PSCA hlg (2700050C12Rik, C530008O16Rik, RIKEN cDNA 2700050C12, RIKEN cDNA 2700050C12 gene); (9) ETBR (Endothelin type B receptor); (10) MSG783 (RNF24, hypothetical protein FLJ20315); (11) STEAP2 [HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein]; (12) TrpM4 [BR22450, FLJ20041, TRPM4, TRPM4B, transient receptor potential cation channel, subfamily M, member 4]; (13) CRIPTO [CR, CR1, CRGF, CRIPTO, TDGF1, teratocarcinoma-derived growth factor]; (14) CD21 (CR2 (complement receptor 2) or C3DR (C3d/Epstein Barr virus receptor) or Hs 73792); (15) CD79b (CD79B, CD79P, IGb (immunoglobulin-associated beta), B29); (16) FcRH2 (IFGP4, IRTA4, SPAP1A (SH-12 domain containing phosphatase anchor protein 1a), SPAP1B, SPAP1C); (17) HER2; (18) NCA; (19) MDP; (20) IL20Rα; (21) Brevican; (22) EphB2R; (23) ASLG659; (24) PSCA; (25) GEDA; (26) BAFF-R (B cell-activating factor receptor, BLyS receptor 3, BR3); (27) CD22 (B-cell receptor CD22-B isoform); (28) CD79a (CD79A, CD79α, immunoglobulin-associated alpha); (29) CXCR5 (Burkitt's lymphoma receptor 1); (30) HLA-DOB (Beta subunit of MHC class II molecule (Ia antigen)); (31) P2X5 (Purinergic receptor P2X ligand-gated ion channel 5); (32) CD72 (B-cell differentiation antigen CD72, Lyb-2); (33) LY64 [Lymphocyte antigen 64 (RP105), type I membrane protein of the leucine rich repeat (LRR) family]; (34) FcRH1 (Fc receptor-like protein 1); (35) IRTA2 (Immunoglobulin superfamily receptor translocation associated 2); (36) TENB2 (putative transmembrane proteoglycan); (37) other selections HGF, EGFR, EGFRvIII, Her2, Her3, IGF-1R, VEGF, VEGFR-1, VEGFR-2, VEGFR-3, Ang2, DII4, NRP1, FGFR, FGFR2, FGFR3, c-Kit, MUC1, MUC16, CD20, CD22, CD27, CD30, CD33, CD40, CD52, CD70, CD79, DDL3, Folate R1, Nectin 4, Trop2, gpNMB, Axl, BCMA, PD-1, PD-L1, PD-L2, CTLA4, BTLA, 4-1BB, ICOS, GITR, OX40, VISTA, TIM-3, LAG-3, KIR, B7.1, B7.2, B7-H2, B7-H3, B7-H4, B7-H6, B7-H7, EphA2, EphA4, EphB2, E-selectin, EpCam, CEA, PSMA, PSA, c-MET, etc.; and (38) TCR/CD3, CD16(Fcγ RIIIa) CD44, CD56, CD69, CD64(Fcγ RI), CD89, CD11b/CD18(CR3) as immune effector cell-related antigens.

In an embodiment of the present disclosure, the antibody may include any antibody without limitation as long as it can be used to prevent and treat proliferative diseases and particularly to treat cancers, and may include a member selected from, for example, alemtuzumab, apolizumab, aselizumab, atlizumab, bapineuzumab, bevacizumab, bivatuzumab mertansine, cantuzumab mertansine, cedelizumab, certolizumab pegol, cetuximab, cidfusituzumab, cidtuzumab, daclizumab, eculizumab, efalizumab, epratuzumab, erlizumab, ertumaxomab, felvizumab, fontolizumab, gemtuzumab, gemtuzumab ozogamicin, ibritumomab tiuxetan, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, panitumumab, pascolizumab, pecfusituzumab, pectuzumab, pertuzumab, pexelizumab, ralivizumab, ranibizumab, reslivizumab, reslizumab, resyvizumab, rituximab, rovelizumab, ruplizumab, sibrotuzumab, siplizumab, sontuzumab, tacatuzumab tetraxetan, tadocizumab, talizumab, tefibazumab, tocilizumab, toralizumab, tositumomab, trastuzumab, tucotuzumab celmoleukin, tucusituzumab, umavizumab, urtoxazumab, and visilizumab, but may not be limited thereto.

In an embodiment of the present disclosure, the linker, used in the art and useful for an antibody-drug conjugate, may be used without limitation. Herein, the linker is a chemical link that attaches the antibody and the drug, and maintains stability when circulated or distributed in the body, but is selectively cut to release the bound drug only when it penetrates into tumor and enters cells. Typically, the linker is composed of an attachment, a spacer and a release, and a new linker can be developed by modifying and/or improving at least one component of an attachment, a spacer and a release of a commercially available linker. In an embodiment of the present disclosure, not only linkers generally used in the art, but also newly developed linkers may be used without limitation as the liker.

In an embodiment of the present disclosure, the linker may be conjugated to a drug by chemical conjugation or enzymatic conjugation, but may not be limited thereto. Specifically, the chemical conjugation may include lysine amide coupling, cysteine coupling or non-natural amino acid incorporation by genetic engineering, but may not be limited thereto. Also, specifically, the enzymatic conjugation may include transpeptidation using sortase, transpeptidation using microbial transglutaminase or n-glycan engineering, but may not be limited thereto.

In an embodiment of the present disclosure, the linker may include at least one cleavable linker, which can be additionally cleaved, or at least one non-cleavable linker, but may not be limited thereto. In an embodiment of the present disclosure, the linker may include a cleavable linker such as a disulfide linker, which is a reducible linker, an enzymatically cleavable linker, a hydrazone linker, which is a chemical-labile linker, a protease-labile linker or a glycosidase-sensitive linker; or a non-cleavable linker such as a non-cleavable bifunctional linker or a non-cleavable spacer linker, but may not be limited thereto.

In an embodiment of the present disclosure, the linker may further include at least one cleavable linker, which can be additionally cleaved, or at least one non-cleavable linker preferably selected from the group consisting of: a hydrazine linker, a thiourea linker, a self-immolative linker, a succinimidyl trans-4-(maleimidylmethyl)cyclohexane-1-carboxylate (SMCC) linker, a disulfide linker, a selenoether linker, an amide linker, a thioether linker and/or a maleimide linker.

In an embodiment of the present disclosure, a person with ordinary skill in the art understands that additional linkers may be suitable. These linkers may not be cleaved or may be cleaved by pH changes, redox potentials or specific intracellular/extracellular enzymes. A cleavable oligopeptide linker includes a protease- or matrix metalloprotease-cleavable linker. It is understood that the linker may include the above combinations. For example, the linker may be a valine-citruline PAB linker.

In an embodiment of the present disclosure, the linker may include N-succinimidyl-4-(2-pyridyldithio)pentanoate (SPP), N-succinimidyl-4-(2-pyridyldithio)butanoate (SPDB), a disulfide linker such as sulfo-SPDB, MDS, DMDS, DSDM, or NDMDS; an enzymatically cleavable linker such as Phe-Lys-PABC, Val-Cit-PABC, Val-Ala-PABC, MHVCBC (valine-citrulline), or MHFKBC (phenylalanine-lysine); a hydrazone linker such as MHH; or a glucosidase-sensitive linker such as GBC (glucuronic acid), GBCDN (glucuronic acid), β-glucuronide linker as a cleavable linker; or may include Mal-PEG-NHS, N-succinimidyl-4-(N-maleimidomethyl)cyclohexane-1-carboxylate (SMCC), Mal-alkane linker, bis-maleimidopolyethyleneglycol (BMPEO), N-(β-maleimidopropyloxy)succinimide ester (BMPS), ε-maleimidocaproic acid N-hydroxysuccinimide ester (EMCS), γ-maleimidobutyric acid N-succinimidyl ester (GMBS), m-maleimidobenzoyl-N-hydroxysuccinimide ester (MBS), 4-(4-N-maleimidophenyl)-butyric acid hydrazide (MPBH), N-succinimidyl 3-(bromoacetamido) propionate (SBAP), N-succinimidyl iodoacetate (SIA), N-succinimidyl-4-(iodoacetyl)-aminobenzoate (SIAB), N-succinimidyl 4-(p-maleimidophenyl)butyrate (SMPB), or succinimidyl-6-(maleimidopropionamido)hexanoate (SMPH) as a non-cleavable linker, but may not be limited thereto.

In an embodiment of the present disclosure, the linker may include a member selected from the followings, but may not be limited thereto:

BMPEO, BMPS, EMCS, GMBS, HBVS, long chain N-succinimidyl 4-(maleimidomethyl)cyclohexane-1-carboxylate (long chain SMCC), MBS, MPBH, SBAP, SIA, SIAB, SMCC, SMPB, SMPH, N-(e-maleimidocaproyloxy) sulfosuccimido ester (sulfo-EMCS), N-(γ-maleimidobutryloxy)sulfosuccinimde ester (sulfo-GMBS], N-(κ-maleimidoundecanoyloxy)sulfosuccinimide ester (sulfo-KMUS], m-maleimidobenzoyl-N-hydroxysulfosuccinimide ester (sulfo-MBS), sulfosuccinimidyl(4-iodo-acetyl)aminobenzoate (sulfo-SIAB), sulfosuccinimidyl 4-(N-maleimidomethyl)cyclohexane-1-carboxylate (sulfo-SMCC), sulfosucciniimidyl 4-(p-maleimidophenyl)butyrate (sulfo-SMPB), succinimidyl-(4-vinylsulfone)benzoate (SVSB), and bis-maleimide reagents: dithiobis-maleimidoethane (DTME), 1,4-bis-maleimidobutane (BMB), 1,4-bismaleimidyl-2,3-dihydroxybutane (BMDB), bis-maleimidohexane (BMH), bis-maleimidoethane (BMOE), 1,8-bis-maleimidodiethyleneglycol [BM(PEO)$_2$], and 1,11-bis-maleimidotriethyleneglycol [BM(PEO)$_3$]; and In an embodiment of the present disclosure, the antibody-drug conjugate of the present disclosure may be a substance having highly potent anticancer effect with IC$_{50}$ to cancer cells in the range of nM or pM, but may not be limited thereto.

In an embodiment of the present disclosure, the linker and the benzoselenophene-based compound may be linked by a peptide bond, but may not be limited thereto.

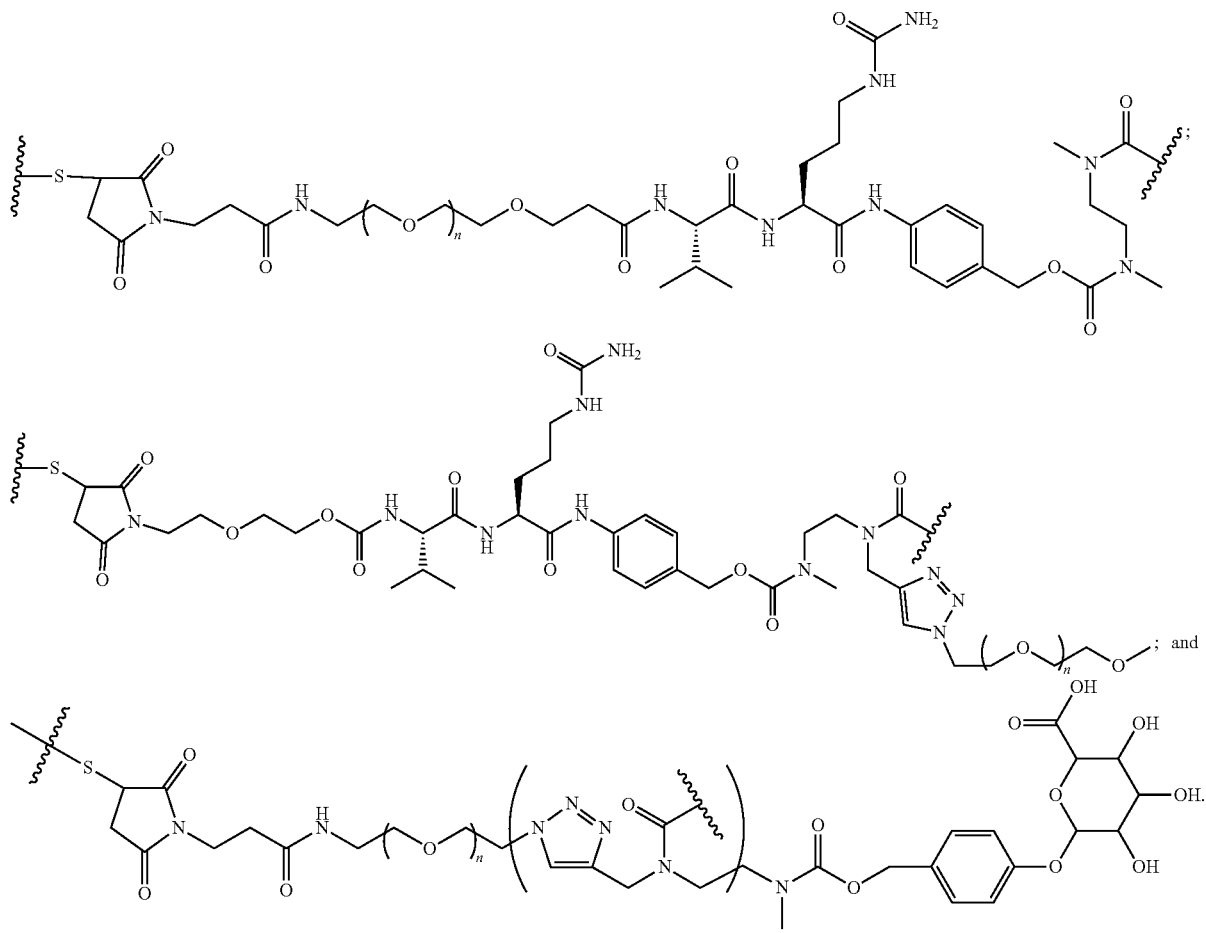

In the above linkers, each of broken lines may indicate a covalent bond to the antibody or the benzoselenophene-based compound, and n may be about 1 to about 1,000.

In an embodiment of the present disclosure, n may be about 1 to about 1,000, about 1 to about 900, about 1 to about 800, about 1 to about 700, about 1 to about 600, about 1 to about 500, about 1 to about 400, about 1 to about 300, about 1 to about 200, about 1 to about 100, about 1 to about 50, about 1 to about 40, about 1 to about 30, about 1 to about 20, about 1 to about 10, about 1 to about 5, or about 1 to about 3, but may not limited thereto. In an embodiment of the present disclosure, n may be about 1 to about 5, or about 1 to about 3.

In an embodiment of the present disclosure, by adjusting n number of polyethylene glycol (PEG) of the linker to form PEG with a molecular weight of, for example, about 1,000 or about 2,000 or to form 4-arm or 8-arm branched PEG, a DNA alkylating derivative containing a benzoselenophene-based compound with increased water solubility can be synthesized and used as an anticancer drug or a precursor thereof, but may not be limited thereto.

In an embodiment of the present disclosure, if the functional groups are substituted, the substituents may include one or more members selected from an acyl group, an amino group (including amino group, mono- and dialkylamino groups, mono- and diarylamino groups and an alkylarylamino group), an acylamino group (including carbamoyl and ureido group), an alkylcarbonyloxy group, an arylcarbonyloxy group, an alkoxycarbonyloxy group, an alkoxycarbonyl group, a carboxy group, carboxylate group, an aminocarbonyl group, mono- and dialkylaminocarbonyl groups, cyano group, azido group, a halogen group, hydroxyl group, nitro group, trifluoromethyl group, thiol group, an alkylthiol group, an arylthiol group, an alkylthiocarbonyl group, a thiocarboxylate group, a lower alkyl group, a lower alkenyl group, a lower alkynyl group, a cycloalkyl group, a heterocycloalkyl group, an aryl group, a heteroaryl group, a lower alkoxy group, an aryloxy group, an aryloxycarbonyloxy group, a benzyloxy group, a benzyl group, a sulfinyl group, an alkylsulfinyl group, a sulfonyl group, a sulfate group, a sulfonate group, a sulfonamide group, a phosphate group, a phosphonate group, a phosphinato group, an oxo group, a guanidine group, imino group and formyl group, but may not be limited thereto.

In an embodiment of the present disclosure, $R^1$ may include a $C_{3-10}$ heterocycloalkyl group or a $C_{3-10}$ heteroaryl group including at least one nitrogen atom, and each of $R^4$ and $R^5$ may be independently hydrogen, methyl group or ethyl group, but may not be limited thereto.

In an embodiment of the present disclosure, X may be F, Cl, Br or I, but may not be limited thereto. Further, in an embodiment of the present disclosure, X may be Cl.

In an embodiment of the present disclosure, a benzoselenophene-based compound of the present disclosure contains two $sp^3$ carbon atoms as a main framework in —$CHR^2CHR^1R^3$, linked to a benzoselenophene host by an amide bond, and thus, the flexibility of the molecule itself can be increased. Further, desirably, $R^1$ may contain various derivatives of a pentagonal or hexagonal ring including N, O or S. In addition, $R^1$ may contain a bicyclic ring with or without a hetero atom, which may facilitate minor groove binding of DNA in an anticancer mechanism.

In an embodiment of the present disclosure, $R^1$ may include pyrrolidinyl group (—$NC_4H_8$), piperidinyl group (—$NC_5H_{10}$), piperazinyl group (—$N_2C_4H_9$), 4-methylpiperazin-1-yl group (—$N_2C_5H_{11}$), morpholino group (—$NOC_4H_8$),

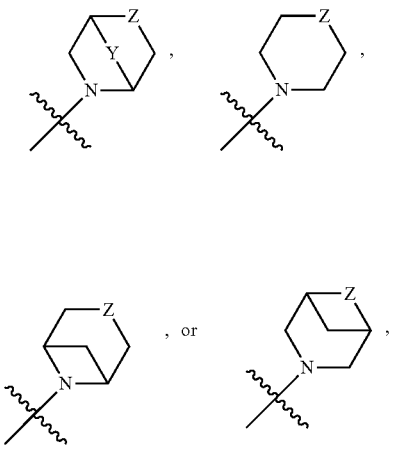

Y may include —$CH_2$— or —$C_2H_4$—, Z may include —CHR—, —NR—, —O—, or —S—, and R may include hydrogen or a $C_{1-3}$ alkyl group, but may not be limited thereto.

In an embodiment of the present disclosure, $R^1$ may be pyrrolidinyl group (—$NC_4H_8$), piperidinyl group (—$NC_5H_{10}$), piperazinyl group (—$N_2C_4H_9$), 4-methylpiperazin-1-yl group (—$N_2C_5H_{11}$), or morpholino group (—$NOC_4H_8$).

In an embodiment of the present disclosure, both $R^2$ and $R^3$ may be hydrogen.

In an embodiment of the present disclosure, each of $R^5$ and $R^6$ may be independently hydrogen, methyl group, ethyl group or a propyl group.

In an embodiment of the present disclosure, the benzoselenophene-based compound may include the following:

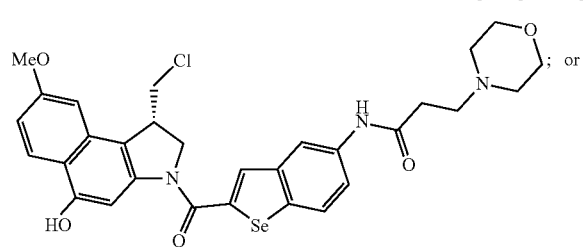

[Compound 3]

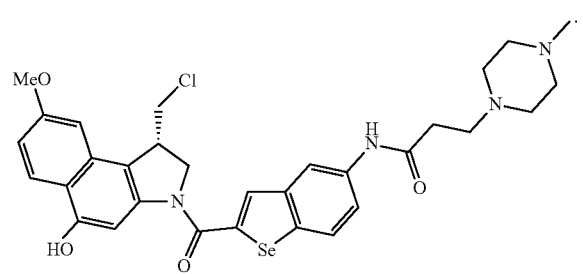

[Compound 4]

In an embodiment of the present disclosure, a bond of the benzoselenophene-based compound of the present disclosure and the linker may be prepared by, for example, the following method, but may not be limited thereto:

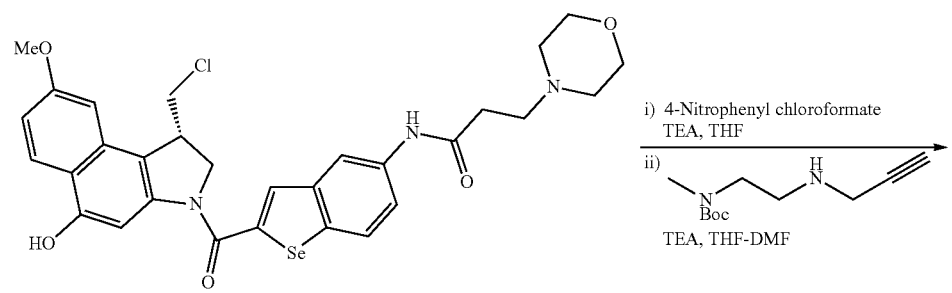

i) 4-Nitrophenyl chloroformate
TEA, THF ii) [structure]
TEA, THF-DMF

3

-continued

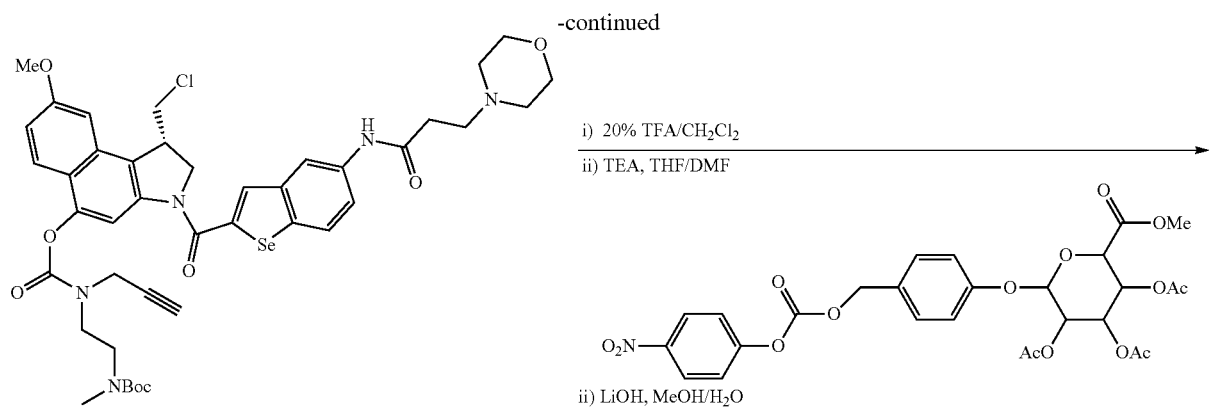

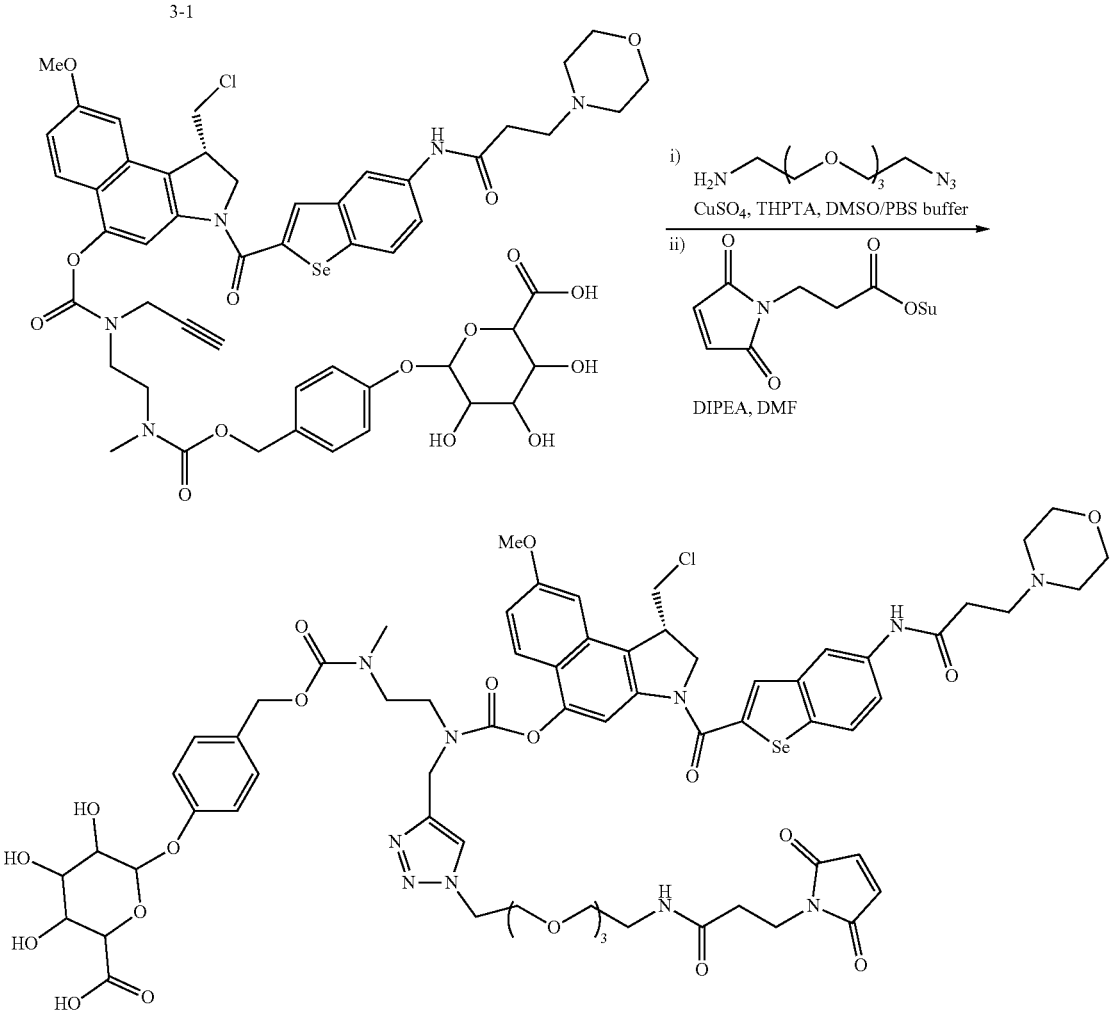

3-3

In an embodiment of the present disclosure, a drug-to-antibody ratio (DAR) of the antibody-drug conjugate may be about 1 to about 8, but may not be limited thereto. In an embodiment of the present disclosure, the DAR of the antibody-drug conjugate may be about 1 to about 8, about 1 to about 6, about 1 to about 5, about 2 to about 8, about 2 to about 6, about 2 to about 5, about 3 to about 8, about 3 to about 6, or about 3 to about 5, but may not be limited thereto. Further, in an embodiment of the present disclosure, the DAR of the antibody-drug conjugate may be about 2 to about 5.

According to a fifth aspect of the present disclosure, there is provided an anticancer composition including the antibody-drug conjugate or the pharmaceutically acceptable salt thereof according to the fourth aspect.

Detailed descriptions on the fifth aspect of the present disclosure, which overlap with those on the first aspect to the fourth aspect of the present disclosure, are omitted hereinafter, but the descriptions of the first aspect to the fourth aspect of the present disclosure may be identically applied to the fifth aspect of the present disclosure, even though they are omitted hereinafter.

In an embodiment of the present disclosure, the anticancer composition may have anticancer activity to at least one disease selected from solid tumor, hematologic malignancy, calorectal cancer, uterine cancer, uterine myoma, meningioma, lung cancer, small cell lung cancer, non-small cell lung cancer, gastrointestinal malignancy, colorectal cancer, intestinal cancer, breast cancer, ovarian cancer, prostate cancer, testis cancer, liver cancer, renal cancer, bladder cancer, pancreatic cancer, brain cancer, brain metastasis, sarcoma, osteogenic sarcoma, Kaposi sarcoma and melanoma, but may not be limited thereto. A pharmaceutical composition according to an embodiment of the present disclosure can be applied to various diseases, not limited to types of cancer, as targets for prevention or treatment.

MODE FOR CARRYING OUT THE INVENTION

Hereinafter, the present disclosure will be explained in more detail with reference to Examples. However, the following Examples are illustrative only for better understanding of the present disclosure but do not limit the present disclosure.

EXAMPLES

1. Synthesis of Intermediate Product (1) Preparation of 5-(3-morpholinopropanamido)benzo[b]selenophene-2-carboxylic Acid (Compound 7)

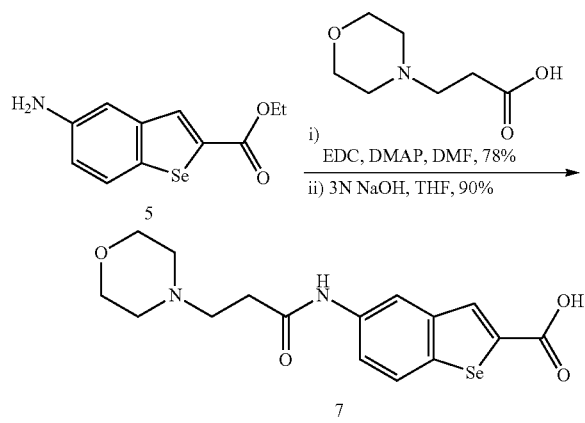

3-morpholinopropanoic acid (3 eq), EDC (3 eq) and DMAP (2 eq) were dissolved in DMF and stirred for 15 minutes and then reacted with (ethyl)(5-amino-benzo[b]selenophene-2-carboxylate) (Compound 5, 1 eq) for 24 hours. After completion of the reaction, methylene chloride (MC)/water was used to separate an MC layer with a separatory funnel and then dried with $MgSO_4$ and filtered. A solvent was removed from the filtrate by a rotary evaporator, followed by column chromatography. Yield: 78%.

$^1$H NMR (500.1 MHz, $CDCl_3$) δ 1.38 (t, 3H, J=7.2), 2.54-2.76 (m, 8H), 3.82 (t, 4H, J=4.4), 4.36 (q, 2H, J=7.2), 7.36 (dd, 1H, J=8.6, 2.1), 7.77 (d, 1H, J=8.6), 8.21 (s, 1H), 8.26 (d, 1H, J=2.2), 10.87 (bs, 1H, NH); $^{13}$C NMR (125.7 MHz, $CDCl_3$) δ 14.4, 32.3, 52.9, 54.2, 61.7, 67.1, 117.6, 119.7, 126.1, 134.2, 136.3, 137.7, 138.8, 141.9, 163.9, 170.5; HRMS (ESI); m/z calcd for $C_{18}H_{22}N_2O_4Se$ [M+]: 410.07; found: 411.0824 [M+H]+.

(Ethyl)(5-(3-(morpholino)propanamido)benzo[b]selenophene-2-carboxylate) (1 eq) obtained in the above-described process was dissolved in methanol and then reacted with 2 mL of 3 N NaOH for 24 hours. After completion of the reaction, 20% HCl was added thereto to adjust pH to acid. Then, a solvent was removed by a rotary evaporator, followed by column chromatography. Yield: 90%.

$^1$H NMR (500.1 MHz, MeOD-$d_4$) δ 2.74-3.11 (m, 8H), 3.81 (s, 4H), 7.48 (d, 1H, J=8.4), 7.87 (d, 1H, J=8.9), 8.08 (s, 1H), 8.21 (s, 1H);
$^{13}$C NMR (125.7 MHz, DMSO-$d_6$) δ 30.2, 51.1, 51.8, 63.2, 117.2, 119.7, 126.4, 133.9, 136.6, 137.8, 138.8, 141.6, 164.7, 167.9; HRMS (ESI); m/z calcd for $C_{16}H_{18}N_2O_4Se$ [M+]: 382.04; found: 383.0512 [M+H]+.

(3) Preparation of 5-(3-(4-methylpiperazin-1-yl)propanamido)benzo[b]selenophene-2-carboxylic Acid (Compound 8)

3-(4-methylpiperazin-1-yl)propanoic acid (3 eq), EDC (3 eq) and DMAP (2 eq) were dissolved in DMF and stirred for 15 minutes and then reacted with (ethyl)(5-amino-benzo[b]selenophene-2-carboxylate) (Compound 5, 1 eq) for 24 hours. After completion of the reaction, methylene chloride (MC)/water was used to separate an MC layer with a separatory funnel and then dried with $MgSO_4$ and filtered. A solvent was removed from the filtrate by a rotary evaporator, followed by column chromatography. Yield: 84%.

$^1$H NMR (500.1 MHz, $CDCl_3$) δ 1.14 (t, 2H, J=7.1), 1.34 (t, 3H, J=7.2), 2.31 (s, 3H), 2.48-2.50 (m, 4H), 2.68-2.70 (m, 4H), 3.41 (q, 2H, J=7.1), 4.31 (q, 2H, J=7.1), 7.34 (d, 1H, J=8.7), 7.72 (d, 1H, J=8.6), 8.16 (s, 1H), 8.22 (s, 1H), 11.02 (bs, 1H, NH);
$^{13}$C NMR (125.7 MHz, $CDCl_3$) δ 14.3, 15.3, 32.6, 46.0, 52.3, 53.6, 55.3, 61.6, 65.8, 117.5, 119.7, 126.0, 134.3, 136.5, 137.5, 138.5, 141.8, 163.8, 170.7; HRMS (ESI); m/z calcd for $C_{19}H_{25}N_3O_3Se$ [M+]: 423.11; found: 424.1139 [M+H]+.

(Ethyl)(5-(3-(4-methylpiperazin-1-yl)propanamido)benzo[b]selenophene-2-carboxylate) (1 eq) obtained in the above-described process was dissolved in methanol and then reacted with 2 mL of 3 N NaOH for 24 hours. After completion of the reaction, 20% HCl was added thereto to adjust pH to acid. Then, a solvent was removed by a rotary evaporator, followed by column chromatography. Yield: 62%.

$^1$H NMR (500.1 MHz, MeOD-$d_4$) δ 2.54-2.58 (m, 2H), 2.66 (s, 3H), 2.77-3.05 (m, 9H), 3.27 (s, 1H), 7.38 (d, 1H, J=8.6), 7.74 (d, 1H, J=8.6) 7.90 (s, 1H), 8.08 (s, 1H);
$^{13}$C NMR (125.7 MHz, DMSO-$d_6$) δ 34.9, 44.0, 51.5, 51.8, 54.2, 54.4, 54.7, 118.8, 120.2, 127.1, 131.3, 137.1, 140.1, 144.2, 149.1, 171.0, 172.5; HRMS (ESI); m/z calcd for $C_{17}H_{21}N_3O_3Se$ [M+]: 395.07; found: 396.0826 [M+H]+.

2. Preparation of Final Product by Reaction of Intermediate Product and Seco-MCBI By using a method known in the art, seco-MCBI (Compound 1) used for the synthesis was synthesized. A process for synthesizing Compounds 3 and 4 by coupling benzoselenophene carboxylic acid to an intermediate product obtained through an acid treatment was performed by the following method:

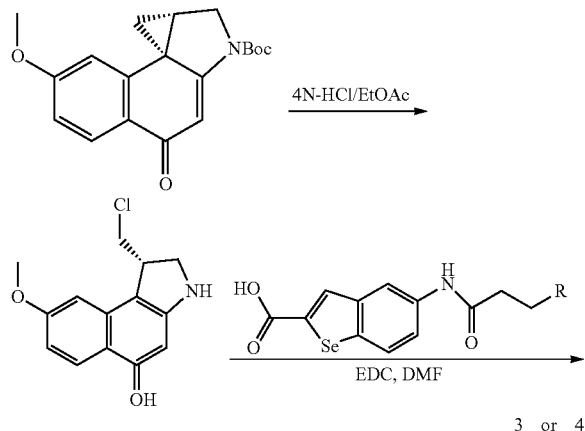

A reaction mixture was prepared by adding, at −78° C., 4 mL of HCl saturated solution in ethyl acetate into a round bottom flask containing seco-MCBI (Compound 1, 30 mg, 0.09 mmol). The reaction mixture was stirred at −78° C. for 30 minutes and then stirred at room temperature for 1 hour. After salt formation was observed through thin layer chromatography (TLC), ethyl acetate was evaporated under nitrogen flux and then completely dried under high vacuum for 1 hour. The produced residue was dissolved in anhydrous DMF (0.2 mL) and added, at 0° C., to a mixture of carboxylic acid (1.1 eq) and EDC (52 mg, 0.27 mmol) represented as Compound 7 or 8 in anhydrous DMF (0.5 mL) and then stirred at 0° C. for 3 hours and stirred at room temperature for 5 hours. After completion of the reaction, the resultant product was diluted with water and extracted with ethyl acetate (3×15 mL). The obtained organic layer was washed with brine and dried with MgSO₄, and filtered and concentrated to produce a crude product. The crude product was purified by column chromatography to obtain a desired product.

3. Analysis Result of Final Product (1) (S)—N-(2-(1-(chloromethyl)-5-hydroxy-8-methoxy-2,3-dihydro-1H-benzo[e]indole-3-carbonyl)benzo[b]selenophen-5-yl)-3-morpholinopropanamide (Compound 3)

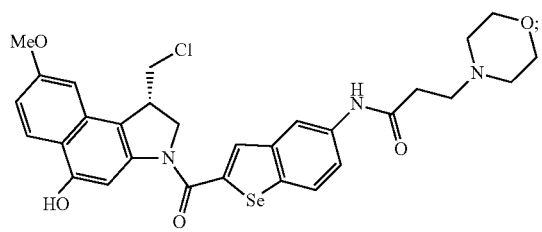 [SMILES: COc1ccc2c(O)cc3c(c2c1)[C@H](CCl)CN3C(=O)c1cc2cc(NC(=O)CCN3CCOCC3)ccc2[se]1]

$^1$H NMR (500.1 MHz, Acetone-d6) δ 10.28 (s, 1H), 9.31 (s, 1H), 8.48 (s, 1H), 8.21 (s, 1H), 8.14 (d, J=9.2 Hz, 1H), 7.99 (m, 1H), 7.76 (brs, 1H), 7.54 (d, J=8.6 Hz, 1H), 7.20 (s, 1H), 7.03 (d, J=9.3 Hz, 1H), 4.76 (t, J=9.5 Hz, 1H), 4.65 (d, J=11.0 Hz, 1H), 4.18 (m, 1H), 4.06 (d, J=11.2 Hz, 1H), 3.95 (s, 3H), 3.82-3.78 (m, 1H), 3.74 (m, 4H), 2.64-2.62 (m, 6H), $^{13}$C NMR (500.1 MHz, CDCl₃⁺ Methanol-d4) δ 171.3, 164.2, 159.7, 155.4, 143.5, 142.7, 142.3, 138.3, 136.6, 132.0, 130.6, 126.2, 126.0, 120.2, 118.9, 118.4, 116.2, 106.5, 101.8, 98.8, 66.7 (2C), 56.7, 55.7, 54.6, 53.4 (2C), 46.2, 45.3, 43.0 HRMS Calcd for (C₃₀H₃₀ClN₃O₅Se) 628.1088 [M+H]+, Observed 628.1087.

4. Synthesis of Mal-Linker-Payload (Compound 3-3)

(1) Synthesis of (S)-1-(chloromethyl)-8-methoxy-3-(5-(3-morpholinopropanamido)benzo[b]selenophene-2-carbonyl)-2,3-dihydro-1H-benzo[e]indol-5-yl (4-nitrophenyl) carbonate (Compound 3-1)

Compound 3 was dissolved in anhydrous THF, followed by filling with N₂ (g). Then, TEA (6 eq) and 4-nitrophenyl chloroformate (4 eq) were added thereinto at 0° C. and reacted at room temperature for 12 hours. After all the THF was evaporated, phenol, pNPC and TEA were removed by ether precipitation. The resultant product was used as a crude in the following reaction.

After the crude was dissolved in DMF/THF (1:4), tert-butyl methyl (2-(prop-2-yn-1-ylamino)ethyl)carbamate (6 eq) and TEA (2 eq) were added thereinto at 0° C. and the reaction was monitored through HPLC. After completion of the reaction, column chromatography was performed with MC/MeOH. Yield: 95%.

$^1$H NMR (500.1 MHz, Acetone) δ 10.123 (s, 1H), 8.446 (s, 1H), 8.126-8.096 (q, 2H), 7.891-7.873 (d, 1H), 7.445-7.428 (d, 1H), 7.204-7.176 (t, 1H), 7.086-7.041 (q, 1H), 4.702-4.4 (m, 3H), 4.323 (s, 1H), 4.211-4.198 (d, 1H), 4.030-3.860 (m, 5H), 3.666-3.650 (q, 6H), 3.546-3.534 (d, 1H), 3.275 (s, 1H), 3.2˜2.8 (m, 6H), 2.676-2.668 (s, 2H), 2.492-2.437 (t, 6H), 2.049-2.005 (m, 3H), 1.464-1.399 (t, 9H); $^{13}$C NMR (500.1 MHz, Acetone) δ 170.94 163.15 160.05 156.53 155.98 155.06 154.78 149.13 148.89 145.41 143.78 143.06 138.08 137.46 132.41 131.10 126.50 125.32 122.68 121.21 119.97 118.81 117.82 109.80 109.74 102.40 80.44 79.92 79.82 74.26 67.47 56.46 55.95 55.07 54.01 47.41 47.09 46.54 46.13 45.63 42.92 38.16 37.65 37.33 35.28 34.92 34.17 28.73 28.67

(2) Synthesis of (2R,3R,4R,5S,6S)-3,4,5-triacetoxy-6-(4-((((2-(((((S)-1-(chloromethyl)-8-methoxy-3-(5-(3-morpholinopropanamido)benzo[b]selenophene-2-carbonyl)-2,3-dihydro-1H-benzo[e]indol-5-yl)oxy)carbonyl)(prop-2-yn-1-yl)amino)ethyl)(methyl)carbamoyl)oxy)methyl)phenoxy)tetrahydro-2H-pyran-2-carboxylic Acid (Compound 3-2)

Compound 3-1 was dissolved in TFA (20% in the presence of methylene chloride as a solvent), and the temperature was increased from 0° C. to room temperature. The reaction was monitored through HPLC, followed by repeated drying with MC. Then, the resultant product was used as a crude in the following reaction.

The crude was dissolved in DMF/THF (1:1), and β-glucuronide linker carbonate (3 eq) and TEA (2 eq) were added thereinto. The reaction was ended when the reactants were removed while monitoring through HPLC. Column chromatography was performed sequentially with ethyl acetate (EA):hexane, EA:methanol (MeOH) and MC:MeOH while monitoring through HPLC. Yield: 60.9%

¹H NMR (500.1 MHz, Acetone) δ 10.9 (s, 1H), 8.4 (d, 1H), 8.1~8.0 (t, 2H), 7.9~7.7 (m, 2H), 7.45~7.32 (t, 1H), 7.3~7.2 (d, 1H), 7.2-7.1 (t, 1H), 7.1~6.85 (m, 2H), 5.5~5.3 (m, 1H), 5.2~4.9 (m, 4H), 4.7~4.5 (m, 2H), 4.5~4.35 (m, 1H), 4.3~4.25 (s, 1H), 4.25~4.1 (s, 1H), 4.0 (d, 1H), 3.9~3.7 (m, 4H), 3.7~3.4 (m, 9H), 3.0~2.8 (m, 4H), 2.7~2.6 (m, 2H), 2.55~2.3 (m, 6H), 1.3~1.1 (m, 4H), 0.85~0.7 (m, 3H)

The compound (1 eq) obtained in the above-described process was dissolved in methanol/water (6:1). LiOH (hydrate, 6 eq) was added thereinto at 0° C. and stirred for 1 hour. The reaction was monitored through HPLC, followed by acidification to pH 3 by addition of acetic acid to produce a solid product. The solid product was filtered and impurities were removed with some acetone and MC. Yield: 99%.

¹H NMR (500.1 MHz, DMSO) δ 10.245 (s, 1H), 8.474 (s, 1H), 8.323 (s, 1H), 8.072-7.970 (q, 2H), 7.867-7.721 (m, 1H), 7.467 (s, 1H), 7.324-7.229 (q, 3H), 7.121 (s, 1H), 6.960-6.861 (t, 2H), 5.411 (s, 1H), 5.208 (s, 1H), 5.029-4.866 (m, 4H), 5.411 (s, 1H), 5.208 (s, 1H), 5.029-4.866 (t, 4H), 4.548-4.533 (d, 1H), 4.400 (s, 2H), 4.225-4.042 (q, 4H), 4.0~3.5 (m, 17H), 2.933 (s, 1H), 2.871 (s, 1H), 2.668-2.656 (d, 3H), 2.441 (s, 3H), 2.086 (s, 3H), 1.140 (s, 1H)

(3) Synthesis of (2R,3R,4R,5S,6S)-3,4,5-triacetoxy-6-(4-((((2-(((((S)-1-(chloromethyl)-8-methoxy-3-(5-(3-morpholinopropanamido)benzo[b]selenophene-2-carbonyl)-2,3-dihydro-1H-benzo[e]indol-5-yl)oxy)carbonyl)((1-(15-(2,5-dioxo-2,5-dihydro-1H-pyrrol-1-yl)-13-oxo-3,6,9-trioxa-12-azapentadecyl)-1H-1,2,3-triazol-4-yl)methyl)amino)ethyl)(methyl)carbamoyl)oxy)methyl)phenoxy)tetrahydro-2H-pyran-2-carboxylic Acid (Compound 3-3)

Compound 3-2 (1 eq) and 2-(2-(2-(2-azidoethoxy)ethoxy)ethoxy)ethanamine (1.5 eq) were dissolved in DMSO, and CuSO₄ (1 eq) and THPTA (1 eq) were dissolved in a buffer solution and then put into the DMSO solution of Compound 3-2. After 20 minutes of adding sodium ascorbate (10 eq) thereinto, the reaction was monitored through HPLC. After completion of the reaction, HPLC was used for separation. Yield: 82%.

¹H NMR (500.1 MHz, DMSO) δ 10.396 (s, 1H), 8.451 (s, 1H), 8.073-8.056 (d, 1H), 8.073-8.056 (q, 2H), 7.728 (m, 3H), 7.511-7.493 (d, 1H), 7.282-7.205 (t, 3H), 7.103-7.085 (d, 1H), 7.000-6.940 (m, 2H), 5.754 (s, 0.5H), 5.1~4.9 (m, 3H), 4.9~4.7 (m, 2H), 4.6~4.5 (s, 4H), 4.4~4.3 (s, 1H), 4.2~3.9 (m, 7H), 3.9~3.8 (s, 3H), 3.75~3.6 (s, 2H), 3.6~3.4 (m, 8H), 3.2~3.1 (s, 9H), 3.0~2.8 (m, 6H), 2.6~2.45 (m, 6H), 2.14~2.05 (s, 4H), 1.8~1.7 (s, 2H), 1.3~1.2 (s, 1H)

After the compound obtained in the above-described process was dissolved in DMF, DIPEA (2 eq) and 2,5-dioxopyrrolidin-1-yl-3-(2,5-dioxo-2,5-dihydro-1H-pyrrol-1-yl)propanoate (1.5 eq) were added thereinto and stirred at room temperature for 2 hours. Yield: 23%

¹H NMR (500.1 MHz, DMSO) δ 10.383 (s, 1H), 8.439 (s, 1H), 8.35-8.3 (d, 1H), 8.073-8.056 (d, 1H), 7.978-7.951 (t, 3H), 7.85-7.6 (m, 1H), 7.510-7.492 (d, 1H), 7.272-7.199 (d, 3H), 7.097-7.080 (t, 1H), 6.995-6.940 (q, 3H), 5.000~4.7 (m, 4H), 4.6~4.5 (m, 4H), 4.45~4.3 (s, 1H), 4.15~3.6 (m, 10H), 3.6~3.2 (m, 9H), 3.2~3.1 (m, 3H), 3.0~2.8 (m, 8H), 2.8~2.7 (s, 3H), 2.7~2.3 (m, 9H), 1.753 (s, 2H), 1.234 (s, 1H)

5. Synthesis of Trastuzumab-Payload (Compound 3, DS-24) Conjugate

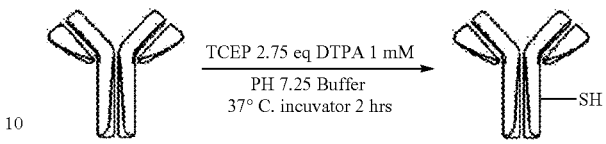

Trastuzumab (TmAb) was used as an antibody and used after purification by gel permeation chromatography. The antibody used has two disulfide bonds connecting HC and LC and two disulfide bonds connecting HC and HC and thus has a total of four interchain disulfide bonds. The antibody was partially reduced with a mild reducing agent tris(2-carboxyethyl) phosphine hydrochloride (TCEP). When the DAR is about 2 to about 5, there is no problem with antigen-antibody reaction and toxicity is high. Therefore, the equivalents of TCEP were adjusted to obtain an average value of DAR about 2 to about 5.

After TmAb (1 eq) was dissolved in PBS (pH=7.25), it was reduced with TCEP (2.75 eq) in an incubator for 30 minutes and subjected to GPC to obtain only the reduced antibody. After the presence or absence of the antibody was checked with a UV spectrometer, 1 mM DTPA was added. Mal-linker-drug (10 eq) was dissolved in DMSO at 5 mg/ml (DMSO 5%, PBS buffer 95%), and 2 equivalents were added each time. After hydrophobic interaction chromatography (HIC) every 30 minutes at 37° C. in the incubator, the Mal-linker-drug was further added. After completion of the reaction, a pure sample was obtained through GPC and formulated by centrifugation with 30 mM histidine, 80 mM trehalose, 0.01% Tween® 20 and 50 mM PBS (pH 6) buffer solution. Then, it was dried in a lyophilizer and stored.

6. Analysis Result of Synthesized Antibody-Drug Conjugate (ADC)

(1) Size Exclusion Chromatography (SEC) Analysis of Trastuzumab-Glucuronide-Compound 3 ADC SEC elutes larger particles first. Thus, if it is eluted earlier than the antibody, the presence or absence of aggregation can be checked. As shown in FIG. 1, as a result of synthesizing the ADC containing Compound 3, aggregation was measured to be 1% or less, which confirms that aggregation hardly occurred.

(2) Hydrophobic Interaction Chromatography (HIC) Analysis of Trastuzumab-Glucuronide-Compound 3 ADC As shown in FIG. 2, samples having a drug to antibody ratio (DAR) of 2, 4, 6 8, and etc. were combined with a sample having a DAR of 0 to appear as one, which means that the linker-drug used has a very high polarity and a good water solubility.

(3) Polymeric Reversed-Phase (PLRC) Analysis of Trastuzumab-Glucuronide-Compound 3 ADC In PLRP, each part of the reduced antibody is reduced (full reduction) and displayed separately on the spectrum, and, thus, it is possible to check which part of the antibody is linked to the linker-drug. As shown in FIG. 3, when the ADC was reduced, it was decomposed into a light chain and a heavy chain. FIG. 3 shows data obtained by quantitatively analyzing not linked to the light chain (L0), one linked to the light chain (L1), not linked to the heavy chain (H0), and one, two and three linked to the heavy chain respectively (H1, H2 and H3). Accordingly, it was confirmed that the DAR was 4.25.

7. Analysis of Anticancer Activity of Compound 3 and ADC Containing the Same

(1) Analysis of in Vitro Cell Line Activity of Compound 3

The activity of Compound 3 was checked by requesting a sample to the NCI NTP program. As shown in FIG. 4, Compound 3 shows a very strong activity with $GI_{50}$ (for Growth Inhibition 50%, activity index in the NCI NTP program) of pM or less in several cell lines, and particularly a remarkably strong activity in non-small lung cancer, CNS cancer, melanoma, and renal cancer (renal cancer).

(2) Analysis of In Vivo Cell Line Activity of Compound 3

According to the analysis results of the in vivo cell line activity of Compound 3 (DS-24), it was confirmed that there was in vivo activity even at a very low concentration as shown in FIGS. 5A to 5C [Cell: B16F10 (Murine melanoma Cell line); Number of cell: 1×10 cell$^5$/mouse; Range of administration: DS-24 (5 ug/kg, 50 ug/kg, 100 ug/kg, IV, twice a week)].

(3) Analysis of Correlation of Compound 3 with Respective Cancer Types in NCI Cell Lines [Sensitivity Difference Between Cancer Types (TGI)]

Based on the results shown in FIG. 6, it was analyzed whether there was any statistical significance in the reactivity depending on cancer types in the cell lines for which the anticancer effect was confirmed by the NCI NTP program. As a result, as shown in FIG. 6, it was confirmed that there was tumor growth inhibition effect against non-small cell lung cancer, CNS cancer and melanoma compared to leukemia. Also, a significant difference in TGI with a p-value of 0.0074 (<0.05) between leukemia and melanoma was confirmed through Wilcoxon's rank sum test. Based on this, it is determined that when Compound 3 is applied to the antibody-drug conjugate, it can exhibit significant efficacy in brain tumor, brain metastases (NSCLC), lung cancer and melanoma.

(4) Activity Analysis of Trastuzumab-Glucuronide-Compound 3 ADC [ADC (DS-24)]

1) Activity Analysis of ADC (DS-24) Depending on Expression of Her2

The ADC synthesized as follows was analyzed to have a DAR of 4.25 and showed similar activity for two formulations (ADC F1 and ADC F2). It can be seen that the activity was excellent in SK-Br-3 and JIMT-1 cell lines in which Her2, the antigen of trastuzumab, was highly expressed, and the activity was low in MCF-7 in which Her2 was low expressed and which was used as a control group. The high activity when treated for 168 hours is considered to be because the linker used is unstable in the MCF-7 cell line.

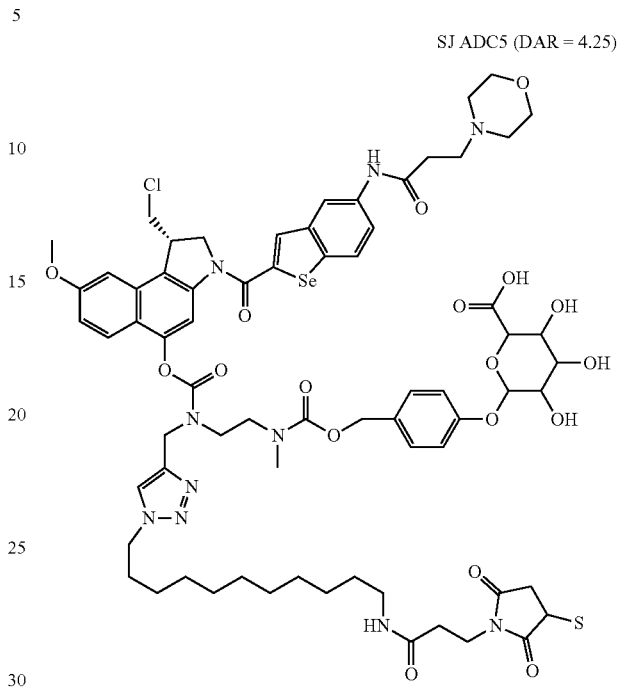

SJ ADC5 (DAR = 4.25)

TABLE 1

|  | SK-Br-3 9 (nM) | | JIMT-1 (nM) | | MCF-7 (nM) | |
| --- | --- | --- | --- | --- | --- | --- |
|  | 96 h | 168 h | 96 h | 168 h | 96 h | 168 h |
| ADC F1 | 0.11 | 0.01 | 2.30 | 0.10 | ▶>10 | 0.12 |
| ADC F2 | 0.12 | 0.01 | 1.27 | 0.08 | ▶>10 | 0.12 |

2) Analysis of Cell Viability of MCF-7 and NCI-N87 Cells Treated with ADC (DS-24)

MCF-7 and NCI-N87 cells were treated with 7 different concentrations of ADC (DS-24) ranging from 0.02 nM to 100 nM for 3 days. FIG. 7A shows nonlinear regression analysis of the dose-response curve, and FIG. 7B shows data of $IC_{50}$ values as a result thereof.

Her2-expressing NCI-N87 cells are sensitive to trastzumab-Compound 3 ADC, while Her2-negative MCF-7 cells are resistant thereto. Specifically, as shown in FIG. 7A and FIG. 7B, MCF-7 and NCI-N87 cells were treated with trastuzumab-glucuronide-Compound 3 ADC and then, intracellular ATP levels were measured to analyze the viability. As a result, NCI-N87 in which the antigen of trastuzumab was expressed showed a high sensitivity, and MCF7 in which the antigen was not expressed showed a low sensitivity.

3) Check of Effect of ADC (DS-24) on Inhibiting BT474 Tumor Spheroid

As shown in FIG. 8A, after formation of a three-dimensional tumor spheroid of the Her2-expressing BT474 cell line in which the antigen of trastuzumab was highly expressed, it was treated with 7 different concentrations of trastuzumab ranging from 0.02 nM to 100 nM and trastuzumab-glucuronide-Compound 3 ADC and observed after 2 weeks. As shown in FIG. 8B and FIG. 8C, a high anticancer activity of ADC (DS-24) was confirmed through nonlinear regression analysis of the dose-response curve, and $IC_{50}$ of trastuzumab was analyzed to be 18.19 nM, and $IC_{50}$ of ADC (DS-24) was analyzed to be 0.23 nM.

4) Effect of ADC (DS-24) in NCI-N87 Xenograft Animal Model and Change in Body Weight After the NCI-N87 cell line in which the antigen of trastuzumab was expressed was xenografted into nude mice, each of trastuzumab and trastuzumab-glucuronide-Compound 2 [ADC (DS-24)] were administered intravenously, followed by observation on anticancer activity. Here, trastuzumab was administered at 5 mg/kg twice per week, and ADC (DS-24) was administered once at a dose of 1 mg/kg and 5 mg/kg.

As shown in FIG. 9A, a group administered with trastuzumab and a group administered with 1 mg/kg of ADC (DS-24) showed a certain degree of tumor formation inhibition, which was not significant. A group administered with 5 mg/kg of ADC (DS-24) showed a non-increase in size of tumor until day 49, which was significant compared to the above-described two groups. As shown in FIG. 9B, the body weight of the mice did not change significantly during the administration period. Therefore, in the group administered with ADC (DS-24), side effects such as serious weight change were not found, and thus, it was confirmed that toxicity did not appear.

5) Toxicity Analysis Through Complete Blood Count (CBC) Test of ADC (DS-24) in NCI-N87 Xenograft Animal Model In the efficacy evaluation of the NCI-N87 xenograft models, blood was collected from the mice when the evaluation of all the subjects were ended, and complete blood count analysis was conducted to determine how the antibody-drug conjugate affects the overall circulation system of a mouse by using a hemocytometer.

As shown in FIG. 10A, the levels of inflammatory cells such as white blood cells (WBC), neutrocytes (NEU), lymphocytes (LYM), and monocytes (MONO) in the control group and the administration groups were in the normal range. As shown in FIGS. 10B i to 10Bvi, anemia-associated values such as red blood cells, hemoglobin, and hematocrit did not show any remarkable findings, and a mean corpuscular volume (MCV), a mean corpuscular hemoglobin (MCH) and a platelet count (PLT) were also checked.

6) Evaluation on Effect of DS-24 Free-Toxin in Cell Line and Brain Tumor Patient-Derived Cell by High-Throughput Screening FIG. 11A, FIG. 11B and FIG. 11C show data confirming the cell viability inhibitory effect of seven types of payloads except Compound 3 (DS-24) on the glioblastoma cell line U87MG, the multiple myeloma cell line KMS11, and the bladder cancer cell line RT112, respectively. Also, FIG. 12A, FIG. 12B, FIG. 12C, FIG. 12D, FIG. 12E and FIG. 12F show data confirming the cell viability inhibitory effect of seven types of payloads except Compound 3 (DS-24) on 6 types of cells derived from a patient with glioblastoma, respectively.

After treatment with the drug diluted to 14 different concentrations based on 20 μM as the highest concentration, it was verified whether the effect is proportional depending on the drug concentration through the concentration graph for two repeated tests. The cell viability was analyzed seven days after drug treatment to calculate $IC_{50}$ that inhibits 50% of the cell viability.

The analyzed $IC_{50}$ values are shown in Table 2 below, and DM1, DM4, MMAE and MMAF showed a remarkable decrease in the cell viability inhibitory effect on cells derived from a patient with glioblastoma compared to KMS11 and RT112. SN-38 and deruxtecan-linker showed similar efficacy in all cells, but had a lower cell viability inhibitory effect than the other payloads. DS-24 showed the highest cell viability inhibitory effect among the compared materials.

In particular, DS-24 showed an $IC_{50}$ value that is about 100 times to about 1,000 times lower than that of the other payloads compared in the cells and cell line (U87MG) derived from a patient with glioblastoma. Therefore, it is considered that the DS-24 drug according to the present disclosure effectively inhibits cell viability of brain tumor and glioblastoma compared to other drugs.

TABLE 2

|  | Dxd-Linker | DS24 | DM1 | DM4 | MMAE | MMAF | SN-38 |
| --- | --- | --- | --- | --- | --- | --- | --- |
| KMS11 (MM) | N.D | 1.22E−11 | 4.41E−11 | 2.29E−11 | 1.53E−10 | 9.14E−08 | 1.69E−07 |
| RT112 (Bladder) | 6.71E−06 | 8.37E−12 | 4.31E−11 | 2.02E−11 | 2.59E−10 | 1.12E−07 | 1.56E−08 |
| U87MG (Glioblastoma) | 1.08E−05 | 3.39E−11 | 1.33E−08 | 1.51E−09 | 3.39E−09 | 3.53E−07 | 6.78E−08 |
| GBM#1 (Glioblastoma, PDC) | 2.47E−05 | 9.80E−10 | 1.33E−07 | 2.98E−08 | 5.16E−08 | 1.69E−05 | 1.28E−07 |
| GBM#2 (Glioblastoma, PDC) | 2.65E−05 | 2.64E−11 | 9.59E−08 | 5.31E−08 | 1.50E−08 | 1.36E−06 | 9.70E−08 |
| GBM#3 (Glioblastoma, PDC) | 7.91E−05 | 3.13E−11 | 4.44E−04 | N.D | 1.67E−04 | 3.11E−05 | 1.31E−07 |
| GBM#4 (Glioblastoma, PDC) | N.D | 2.15E−10 | 9.21E−08 | 8.15E−09 | 5.33E−08 | 8.86E−06 | 1.46E−07 |

8. Analysis of Anticancer Activity of Compound 3 Compared to Compound 2

Although the present inventors have previously prepared the following Compound 2 and analyzed the anticancer activity thereof, it was confirmed that the following Compound 3 according to the present disclosure has significantly superior anticancer activity compared to Compound 2. Specifically, cell growth inhibition assay was performed:

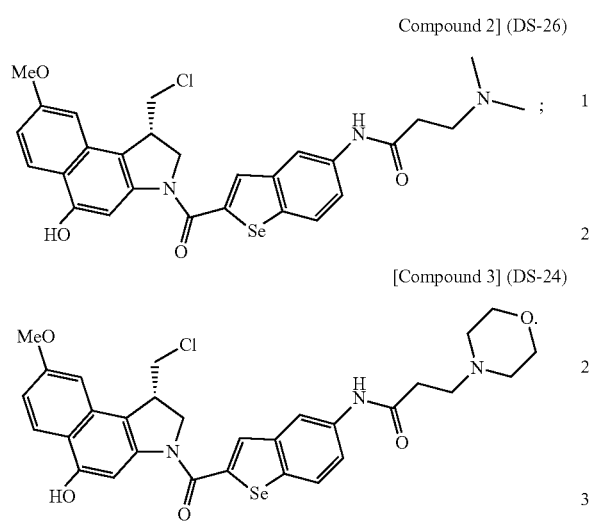

Her2-positive human gastric cancer cells NCI-N87 and human ovarian cancer cells SK-OV3 purchased from the American Type Culture Collection (ATCC; Manassas, VA, USA) were seeded into a 384-well plate at 500 cells per well. After plating for 2 hours, the cells were treated in quadruplicate with toxins in 5-fold and 14-point serial dilution series. After 3 days of incubation at 37° C. in a 5% $CO_2$ humidified incubator, cell viability was checked using an adenosine triphosphate monitoring system based on firefly luciferase (ATPlite™ 1step, PerkinElmer, MA, USA). $IC_{50}$ values were calculated as an average of four quadruplicated tests (GraphPad Prism 5.0, CA, and USA). Specific experimental values are shown in Table 3 below. FIG. 13A and FIG. 13B are graphs showing the cell viability of NCI-N87 depending on the concentrations of DS-24 and DS-26, respectively, and FIG. 14A and FIG. 14B are graphs showing the cell viability of SK-OV3 depending on the concentrations of DS-24 and DS-26, respectively.

TABLE 3

|  | $IC_{50}$ (pM)/AUC NCI-N87 | $IC_{50}$ (pM)/AUC SK-OV3 |
|---|---|---|
| Compound 2 (DS-26) | 55/477 | 42/481 |
| Compound 3 (DS-24) | 0.05/277 | 0.01/160 |

(* AUC : Area under the curve)

The above description of the present disclosure is provided for the purpose of illustration, and it would be understood by those skilled in the art that various changes and modifications may be made without changing technical conception and essential features of the present disclosure. Thus, it is clear that the above-described examples are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. A benzoselenophene-based compound, represented by the following Chemical Formula 1:

[Chemical Formula 1]

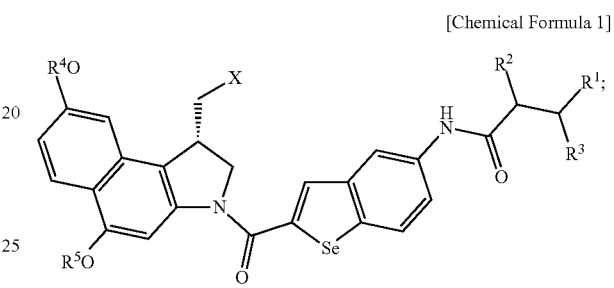

in the above Chemical Formula 1, $R^1$ is a substituted or unsubstituted $C_{3-10}$ heterocycloalkyl group including at least one nitrogen atom or a substituted or unsubstituted $C_{3-10}$ heteroaryl group including at least one nitrogen atom, each of $R^2$ and $R^3$ is independently hydrogen, fluorine, chlorine, bromine, iodine, or a substituted or unsubstituted $C_{1-5}$ alkyl group, each of $R^4$ and $R^5$ is independently hydrogen, or a substituted or unsubstituted $C_{1-5}$ alkyl group, the heterocycloalkyl group and the heteroaryl group further include at least one hetero atom selected from O and S or not, X is halogen, and if one or more of R1, R2, R3, R4 or R5 is substituted, the substituent is one or more members selected from the group consisting of an acyl group, an amino group, an acylamino group, an alkylcarbonyloxy group, an arylcarbonyloxy group, an alkoxycarbonyloxy group, an alkoxycarbonyl group, a carboxy group, a carboxylate group, an aminocarbonyl group, a mono- and dialkylaminocarbonyl groups, a cyano group, an azido group, a halogen group, a hydroxyl group, a nitro group, a trifluoromethyl group, a thiol group, an alkylthiol group, an arylthiol group, an alkylthiocarbonyl group, a thiocarboxylate group, a lower alkyl group, a lower alkenyl group, a lower alkynyl group, a cycloalkyl group, a heterocycloalkyl group, an aryl group, a heteroaryl group, a lower alkoxy group, an aryloxy group, an aryloxycarbonyloxy group, a benzyloxy group, a benzyl group, a sulfinyl group, an alkylsulfinyl group, a sulfonyl group, a sulfate group, a sulfonate group, a sulfonamide group, a phosphate group, a phosphonate group, a phosphinato group, an oxo group, a guanidine group, an imino group and a formyl group.

2. The benzoselenophene-based compound of claim 1, wherein each of $R^4$ and $R^5$ is independently hydrogen, methyl group or ethyl group.

3. The benzoselenophene-based compound of claim 1,
wherein $R^1$ includes pyrrolidinyl group, piperidinyl group, piperazinyl group, 4-methylpiperazin-1-yl group, morpholino group,

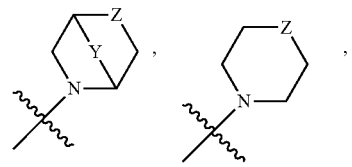

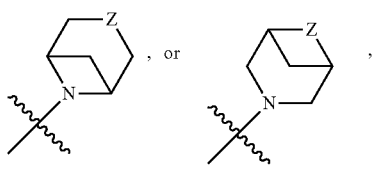

Y includes —$CH_2$— or —$C_2H_4$—,
Z includes —CHR—, —NR—, —O—, or —S—, and
R includes hydrogen or a $C_{1-3}$ alkyl group.

4. The benzoselenophene-based compound of claim 1,
wherein the benzoselenophene-based compound is Compound 3 or Compound 4:

[Compound 3]

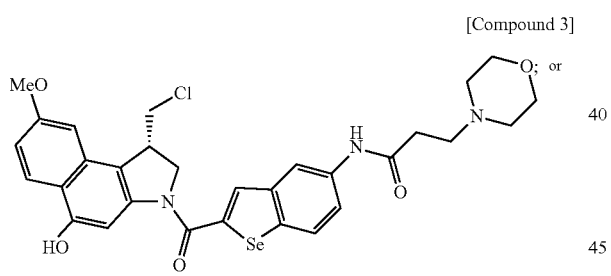

[Compound 4]

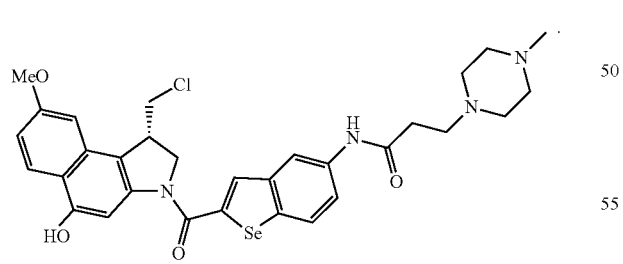

5. A pharmaceutical composition, comprising a benzoselenophene-based compound represented by the following Chemical Formula 1 or a pharmaceutically acceptable salt thereof, the pharmaceutical composition is for treating proliferative diseases wherein the proliferative diseases include at least one selected from the group consisting of cancer, leukaemia, psoriasis, bone diseases, fibroblastic disorders and atherosclerosis:

[Chemical Formula 1]

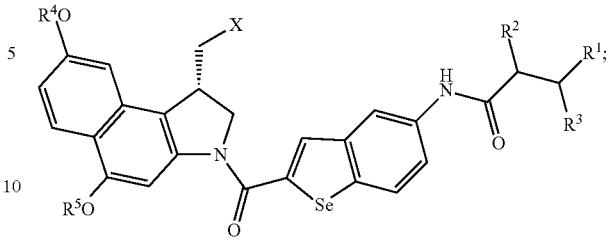

in the above Chemical Formula 1,
$R^1$ is a substituted or unsubstituted $C_{3-10}$ heterocycloalkyl group including at least one nitrogen atom or a substituted or unsubstituted $C_{3-10}$ heteroaryl group including at least one nitrogen atom,
each of $R^2$ and $R^3$ is independently hydrogen, fluorine, chlorine, bromine, iodine, or a substituted or unsubstituted $C_{1-5}$ alkyl group,
each of $R^4$ and $R^5$ is independently hydrogen, or a substituted or unsubstituted $C_{1-5}$ alkyl group,
the heterocycloalkyl group and the heteroaryl group further include at least one hetero atom selected from O and S or not,
X is halogen, and
if one or more of R1, R2, R3, R4 or R5 is substituted, the substituent is one or more members selected from the group consisting of an acyl group, an amino group, an acylamino group, an alkylcarbonyloxy group, an arylcarbonyloxy group, an alkoxycarbonyloxy group, an alkoxycarbonyl group, a carboxy group, a carboxylate group, an aminocarbonyl group, a mono- and dialkylaminocarbonyl groups, a cyano group, an azido group, a halogen group, a hydroxyl group, a nitro group, a trifluoromethyl group, a thiol group, an alkylthiol group, an arylthiol group, an alkylthiocarbonyl group, a thiocarboxylate group, a lower alkyl group, a lower alkenyl group, a lower alkynyl group, a cycloalkyl group, a heterocycloalkyl group, an aryl group, a heteroaryl group, a lower alkoxy group, an aryloxy group, an aryloxycarbonyloxy group, a benzyloxy group, a benzyl group, a sulfinyl group, an alkylsulfinyl group, a sulfonyl group, a sulfate group, a sulfonate group, a sulfonamide group, a phosphate group, a phosphonate group, a phosphinato group, an oxo group, a guanidine group, an imino group and a formyl group.

6. The pharmaceutical composition of claim 5,
wherein the benzoselenophene-based compound or the pharmaceutically acceptable salt thereof is a prodrug.

7. The pharmaceutical composition of claim 5,
wherein the cancer includes at least one selected from solid tumor, hematologic malignancy, calorectal cancer, uterine cancer, uterine myoma, meningioma, lung cancer, small cell lung cancer, non-small cell lung cancer, gastrointestinal malignancy, colorectal cancer, intestinal cancer, breast cancer, ovarian cancer, prostate cancer, testis cancer, liver cancer, renal cancer, bladder cancer, pancreatic cancer, brain cancer, brain metastasis, sarcoma, osteogenic sarcoma, Kaposi sarcoma and melanoma.

8. The pharmaceutical composition of claim 5,
wherein each of $R^4$ and $R^5$ is independently hydrogen, methyl group or ethyl group.

9. The pharmaceutical composition of claim 5,
wherein R¹ includes pyrrolidinyl group, piperidinyl group, piperazinyl group, 4-methylpiperazin-1-yl group, morpholino group,

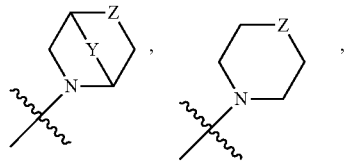

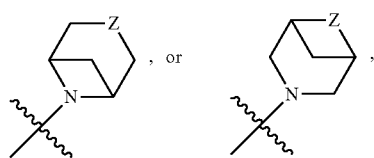

Y includes —CH₂— or —C₂H₄—,
Z includes —CHR—, —NR—, —O—, or —S—, and
R includes hydrogen or a C₁₋₃ alkyl group.

10. The pharmaceutical composition of claim 5,
wherein the benzoselenophene-based compound is Compound 3 or Compound 4:

[Compound 3]

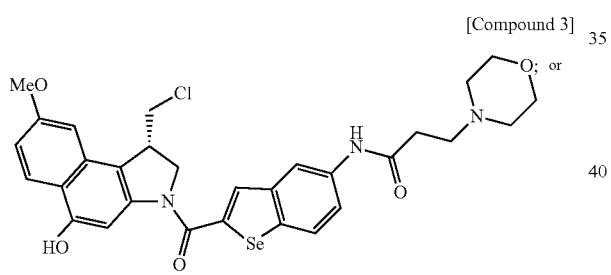

[Compound 4]

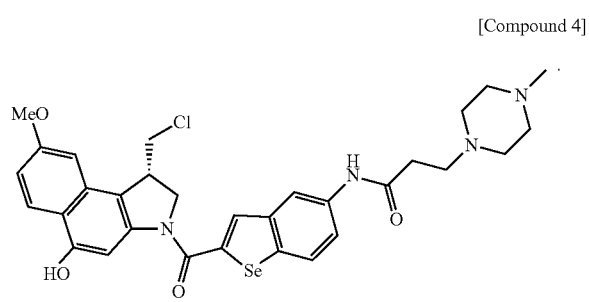

11. An antibody-drug conjugate or a pharmaceutically acceptable salt thereof, comprising:
an antibody;
a linker; and
a benzoselenophene-based compound represented by the following Chemical Formula 1 or a pharmaceutically acceptable salt thereof:

[Chemical Formula 1]

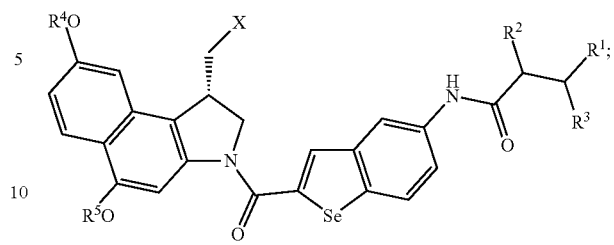

in the above Chemical Formula 1,
R¹ is a substituted or unsubstituted C₃₋₁₀ heterocycloalkyl group including at least one nitrogen atom or a substituted or unsubstituted C₃₋₁₀ heteroaryl group including at least one nitrogen atom,
each of R² and R³ is independently hydrogen, fluorine, chlorine, bromine, iodine, or a substituted or unsubstituted C₁₋₅ alkyl group,
each of R⁴ and R⁵ is independently hydrogen, or a substituted or unsubstituted C₁₋₅ alkyl group,
the heterocycloalkyl group and the heteroaryl group further include at least one hetero atom selected from O and S or not,
X is halogen, and
if one or more of R1, R2, R3, R4 or R5 is substituted, the substituent is one or more members selected from the group consisting of an acyl group, an amino group, an acylamino group, an alkylcarbonyloxy group, an arylcarbonyloxy group, an alkoxycarbonyloxy group, an alkoxycarbonyl group, a carboxy group, a carboxylate group, an aminocarbonyl group, a mono- and dialkylaminocarbonyl groups, a cyano group, an azido group, a halogen group, a hydroxyl group, a nitro group, a trifluoromethyl group, a thiol group, an alkylthio group, an arylthiol group, an alkylthiocarbonyl group, a thiocarboxylate group, a lower alkyl group, a lower alkenyl group, a lower alkynyl group, a cycloalkyl group, a heterocycloalkyl group, an aryl group, a heteroaryl group, a lower alkoxy group, an aryloxy group, an aryloxycarbonyloxy group, a benzyloxy group, a benzyl group, a sulfinyl group, an alkylsulfinyl group, a sulfonyl group, a sulfate group, a sulfonate group, a sulfonamide group, a phosphate group, a phosphonate group, a phosphinato group, an oxo group, a guanidine group, an imino group and a formyl group.

12. The antibody-drug conjugate or a pharmaceutically acceptable salt thereof of claim 11,
wherein the antibody-drug conjugate or a pharmaceutically acceptable salt thereof is a prodrug.

13. The antibody-drug conjugate or a pharmaceutically acceptable salt thereof of claim 11,
wherein the antibody includes an antibody, an antibody variant or antigen-biding fragments thereof immunospecific to a proliferative disease.

14. The antibody-drug conjugate or a pharmaceutically acceptable salt thereof of claim 13 wherein the proliferative diseases include at least one selected from the group consisting of, cancer, leukaemia, psoriasis, bone diseases, fibroblastic disorders and atherosclerosis.

15. The antibody-drug conjugate or a pharmaceutically acceptable salt thereof of claim 14,
wherein the cancer includes at least one selected from solid tumor, hematologic malignancy, calorectal cancer, uterine cancer, uterine myoma, meningioma, lung cancer, small cell lung cancer, non-small cell lung cancer, gastrointestinal malignancy, colorectal cancer, intestinal cancer, breast cancer, ovarian cancer, prostate cancer, testis cancer, liver cancer, renal cancer, bladder cancer, pancreatic cancer, brain cancer, brain metastasis, sarcoma, osteogenic sarcoma, Kaposi sarcoma and melanoma.

16. The antibody-drug conjugate or a pharmaceutically acceptable salt thereof of claim 11,
wherein the antibody includes a member selected from alemtuzumab, apolizumab, aselizumab, atlizumab, bapineuzumab, bevacizumab, bivatuzumab mertansine, cantuzumab mertansine, cedelizumab, certolizumab pegol, cetuximab, cidfusituzumab, cidtuzumab, daclizumab, eculizumab, efalizumab, epratuzumab, erlizumab, ertumaxomab, felvizumab, fontolizumab, gemtuzumab, gemtuzumab ozogamicin, ibritumomab tiuxetan, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, panitumumab, pascolizumab, pecfusituzumab, pectuzumab, pertuzumab, pexelizumab, ralivizumab, ranibizumab, reslivizumab, reslizumab, resyvizumab, rituximab, rovelizumab, ruplizumab, sibrotuzumab, siplizumab, sontuzumab, tacatuzumab tetraxetan, tadocizumab, talizumab, tefibazumab, tocilizumab, toralizumab, tositumomab, trastuzumab, tucotuzumab celmoleukin, tucusituzumab, umavizumab, urtoxazumab, and visilizumab.

17. The antibody-drug conjugate or a pharmaceutically acceptable salt thereof of claim 11,
wherein the linker includes a cleavable linker or a non-cleavable linker.

18. The antibody-drug conjugate or a pharmaceutically acceptable salt thereof of claim 11,
wherein each of $R^4$ and $R^5$ is independently hydrogen, methyl group or ethyl group.

19. The antibody-drug conjugate or a pharmaceutically acceptable salt thereof of claim 11,
wherein $R^1$ includes pyrrolidinyl group, piperidinyl group, piperazinyl group, 4-methylpiperazin-1-yl group, morpholino group,

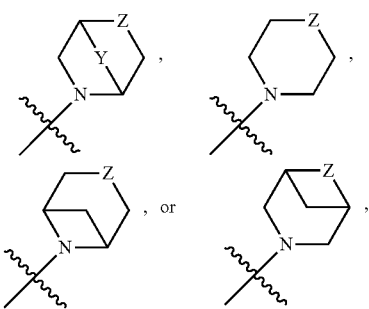

Y includes —$CH_2$— or —$C_2H_4$—,
Z includes —CHR—, —NR, —O—, or —S—, and
R includes hydrogen or a $C_{1-3}$ alkyl group.

20. The antibody-drug conjugate or a pharmaceutically acceptable salt thereof of claim 11,
wherein the benzoselenophene-based compound is Compound 3 or Compound 4:

[Compound 3]

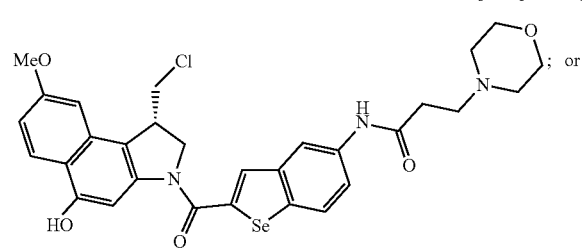

; or

[Compound 4]

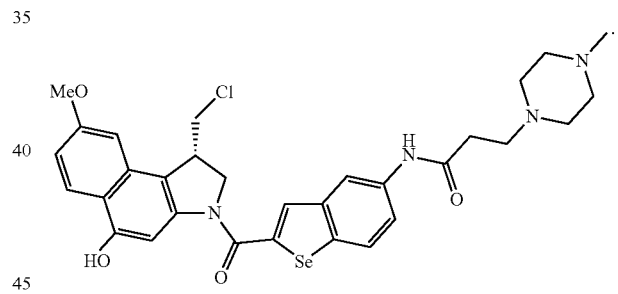

* * * * *